(12) United States Patent
Fox et al.

(10) Patent No.: US 9,984,455 B1
(45) Date of Patent: May 29, 2018

(54) ORGANISM GROWTH PREDICTION SYSTEM USING DRONE-CAPTURED IMAGES

(71) Applicant: Hana Resources, Inc., Lake Forest, CA (US)

(72) Inventors: Andrew John Fox, Irvine, CA (US); Michelle Caruana, Laguna Hills, CA (US)

(73) Assignee: Hana Resources, Inc., Lake Forest, CA (US)

( * ) Notice: Subject to any disclaimer, the term of this patent is extended or adjusted under 35 U.S.C. 154(b) by 0 days. days.

(21) Appl. No.: 15/798,132

(22) Filed: Oct. 30, 2017

Related U.S. Application Data

(60) Provisional application No. 62/515,367, filed on Jun. 5, 2017, provisional application No. 62/545,273, filed (Continued)

(51) Int. Cl.

| | |
|---|---|
| *G06K 9/00* | (2006.01) |
| *G06T 7/00* | (2017.01) |
| *G06T 11/60* | (2006.01) |
| *H04N 5/33* | (2006.01) |
| *A01G 25/16* | (2006.01) |
| *A01G 7/04* | (2006.01) |
| *A01G 7/06* | (2006.01) |
| *B64C 39/02* | (2006.01) |

(Continued)

(52) U.S. Cl.
CPC .............. *G06T 7/001* (2013.01); *A01G 7/045* (2013.01); *A01G 7/06* (2013.01); *A01G 25/16* (2013.01); *B64C 39/024* (2013.01); *B64D 47/08* (2013.01); *G06T 11/60* (2013.01); *G08G 5/0069* (2013.01); *H04N 5/247* (2013.01); *H04N 5/33* (2013.01); *B64C 2201/024* (2013.01); *B64C 2201/123* (2013.01); *B64C 2201/127* (2013.01); *B64C 2201/141* (2013.01); *G06T 2207/30188* (2013.01)

(58) Field of Classification Search
None
See application file for complete search history.

(56) References Cited

U.S. PATENT DOCUMENTS 5,764,819 A * 6/1998 Orr ........................ A01G 7/00
348/144
7,298,869 B1 * 11/2007 Abernathy ........... G06K 9/0063
324/323

(Continued)

*Primary Examiner* — Shervin Nakhjavan
(74) *Attorney, Agent, or Firm* — Knobbe Martens Olson & Bear LLP

(57) ABSTRACT

A plant growth measurement and prediction system uses drone-captured images to measure the current growth of particular plant species and/or to predict future growth of the plant species. For example, the system instructs a drone to fly along a flight path and capture images of the land below. The captured images may include both thermographic images and high-resolution images. The system processes the images to create an orthomosaic image of the land, where each pixel in the orthomosaic image is associated with a brightness temperature. The system then uses plant species to brightness temperature mappings and the orthomosaic image to identify current plant growth. The system generates a diagnostic model using the orthomosaic image to then predict future plant growth.

28 Claims, 14 Drawing Sheets

Related U.S. Application Data on Aug. 14, 2017, provisional application No. 62/563,276, filed on Sep. 26, 2017.

(51) Int. Cl.
*B64D 47/08* (2006.01)
*G08G 5/00* (2006.01)
*H04N 5/247* (2006.01)

(56) References Cited

U.S. PATENT DOCUMENTS

| | | | |
|---|---|---|---|
| 9,265,204 B2* | 2/2016 | Younis | A01G 25/16 |
| 9,504,213 B2* | 11/2016 | Levine | A01G 25/16 |
| 9,811,849 B2* | 11/2017 | Bursey | G06Q 30/0621 |
| 9,880,537 B2* | 1/2018 | Mewes | G05B 19/042 |
| 2001/0036295 A1* | 11/2001 | Hendrickson | G01J 3/2803 |
| | | | 382/110 |
| 2014/0146173 A1* | 5/2014 | Joyce | G01C 11/04 |
| | | | 348/144 |
| 2015/0022656 A1* | 1/2015 | Carr | G06K 9/0063 |
| | | | 348/117 |
| 2016/0300375 A1* | 10/2016 | Beckett | G06T 3/4092 |
| 2016/0307373 A1* | 10/2016 | Dean | G06T 19/006 |
| 2017/0124745 A1* | 5/2017 | Christ | G06T 11/60 |
| 2017/0349635 A1* | 12/2017 | Gil | A01H 5/10 |

* cited by examiner

ORGANISM GROWTH PREDICTION SYSTEM USING DRONE-CAPTURED IMAGES

CROSS-REFERENCE TO RELATED APPLICATIONS

This application claims priority under 35 U.S.C. § 119(e) to U.S. Provisional Patent Application No. 62/515,367, entitled "ORGANISM GROWTH PREDICTION SYSTEM USING DRONE-CAPTURED IMAGES" and filed on Jun. 5, 2017, to U.S. Provisional Patent Application No. 62/545,273, entitled "ORGANISM GROWTH PREDICTION SYSTEM USING DRONE-CAPTURED IMAGES" and filed on Aug. 14, 2017, and to U.S. Provisional Patent Application No. 62/563,276, entitled "ORGANISM GROWTH PREDICTION SYSTEM USING DRONE-CAPTURED IMAGES" and filed on Sep. 26, 2017, each of which is hereby incorporated by reference herein in its entirety.

BACKGROUND

Occasionally, land becomes damaged or degraded due to human actions, such as construction, contamination, the introduction of invasive species, and/or the like. This damage or degradation can negatively affect the health of native vegetation and/or the population of endangered species. In fact, such damage or degradation can negatively impact humans. For example, disturbing the natural habitat of the land can increase the risk of flooding, reduce access to clean water, or reduce recreational opportunities. Thus, a land owner or a government entity may attempt to restore the land to its natural habitat by reintroducing native vegetation and attempting to recreate the original native vegetation coverage.

As part of the habitat restoration process, it may be important track the health and growth of the native vegetation at a site over time. Currently, this task is performed by a biologist. For example, the biologist may visit the site, collect plant samples from a specific area or portion of the site (e.g., along a transect), analyze the samples in a lab to identify the plant species that were present (e.g., by visually inspecting the features of the collected samples and comparing those features to the features of known plant species, by running a DNA test and comparing the results to the DNA of known plant species, etc.), and estimate a status of the growth of a particular plant species in the entire site based on the analysis. However, because the biologist takes samples from just a portion of the site, the plant growth estimates are often subjective and ultimately imprecise.

SUMMARY

The systems, methods, and devices described herein each have several aspects, no single one of which is solely responsible for its desirable attributes. Without limiting the scope of this disclosure, several non-limiting features will now be discussed briefly.

One aspect of the disclosure provides a system for predicting plant growth. The system comprises an unmanned aerial vehicle, wherein the unmanned aerial vehicle comprises a first camera and a second camera. The system further comprises a computing system comprising one or more computing devices, wherein the computing system is configured to communicate with the unmanned aerial vehicle and configured with specific computer-executable instructions to: instruct the unmanned aerial vehicle to capture a first set of images using the first camera and a second set of images using the second camera while flying along a flight path; receive the first set of images and the second set of images from the unmanned aerial vehicle; generate an orthomosaic image using the first set of images and the second set of images; process the orthomosaic image to identify a percentage of a land parcel that is covered by a first plant species; generate a diagnostic model using the identified percentage of the land parcel that is covered by the first plant species; and predict future plant growth using the diagnostic model.

The system of the preceding paragraph can include any sub-combination of the following features: where the computing system is further configured with specific computer-executable instructions to: combine the first set of images according to geographic coordinates associated with each image in the first set to form a combined first image, and orthorectify the combined first image and the combined second image to generate the orthomosaic image; where the first camera comprises a thermal imaging camera; where each pixel in each image in the first set corresponds to a brightness temperature, and wherein each pixel in the orthomosaic image corresponds to a brightness temperature; where the computing system is further configured with specific computer-executable instructions to: retrieve data indicating that the first plant species is associated with a first brightness temperature, process the orthomosaic image to identify that a first set of pixels of the orthomosaic image correspond to the first brightness temperature, determine that the first set of pixels are a first percentage of a total number of pixels in the orthomosaic image, and determine that the percentage of the land parcel that is covered by the first plant species equals the first percentage; where the computing system is further configured with specific computer-executable instructions to: retrieve data indicating that the first plant species is associated with a first brightness temperature, process the orthomosaic image to identify that a first pixel of the orthomosaic image corresponds to the first brightness temperature, and identify a first plant at the first pixel, wherein the first plant is an individual plant of the first plant species; where the computing system is further configured with specific computer-executable instructions to identify a health of a plant at a first pixel of the orthomosaic image based on the brightness temperature of the first pixel; where the identified percentage of the land parcel that is covered by the first plant species is the percentage of the land parcel that is covered by the first plant species at a first time, and wherein the computing system is further configured with specific computer-executable instructions to: retrieve data indicating a second percentage of the land parcel that was covered by the first plant species at a second time before the first time, and perform a linear regression analysis on at least one of the percentage, the second percentage, the first time, and the second time to generate the diagnostic model; where the computing system is further configured with specific computer-executable instructions to identify a predicted time when a percentage of the land parcel that is covered by the first plant species equals a desired percentage; where the computing system is further configured with specific computer-executable instructions to: modify the orthomosaic image to indicate a portion of the land parcel at which the first plant species needs to grow such that a percentage of the land parcel that is covered by the first plant species equals a desired percentage, and transmit the modified orthomosaic image to a user device; where the computing system is further configured with specific computer-executable instructions to: receive flight path parameters from a user device over a network, and instruct the unmanned aerial vehicle to capture the first set of images using the first camera and the second set of images using the second camera while flying along a flight path in a manner defined by the flight path parameters; and where the flight path parameters comprise at least one of geographic coordinates, waypoints, flight length, flight time, speed, altitude, camera shooting angle, camera capture mode, or camera resolution.

Another aspect of the disclosure provides a computer-implemented method of predicting plant growth. The computer-implemented method comprises, as implemented by one or more computing devices configured with specific computer-executable instructions: instructing an aerial vehicle to commence a flight such that the aerial vehicle captures a first set of images using a first camera and captures a second set of images using a second camera; receiving the first set of images and the second set of images from the aerial vehicle; generating an orthomosaic image using the first set of images and the second set of images; processing the orthomosaic image to identify a percentage of a land parcel that is covered by a first plant species; generating a diagnostic model using the identified percentage of the land parcel that is covered by the first plant species; and predicting future plant growth using the diagnostic model.

The computer-implemented method of the preceding paragraph can include any sub-combination of the following features: where generating an orthomosaic image using the first set of images and the second set of images further comprises: combining the first set of images according to geographic coordinates associated with each image in the first set to form a combined first image, combining the second set of images according to geographic coordinates associated with each image in the second set to form a combined second image, and orthorectifying the combined first image and the combined second image to generate the orthomosaic image; where the first camera comprises a thermal imaging camera; where each pixel in each image in the first set corresponds to a brightness temperature, and wherein each pixel in the orthomosaic image corresponds to a brightness temperature; where processing the orthomosaic image to identify a percentage of a land parcel that is covered by a first plant species further comprises: retrieving data indicating that the first plant species is associated with a first brightness temperature, processing the orthomosaic image to identify that a first set of pixels of the orthomosaic image correspond to the first brightness temperature, determining that the first set of pixels are a first percentage of a total number of pixels in the orthomosaic image, and determining that the percentage of the land parcel that is covered by the first plant species equals the first percentage; where the computer-implemented method further comprises: retrieving data indicating that the first plant species is associated with a first brightness temperature, processing the orthomosaic image to identify that a first pixel of the orthomosaic image corresponds to the first brightness temperature, and identifying a first plant at the first pixel, wherein the first plant is an individual plant of the first plant species; where the computer-implemented method further comprises identifying a health of a plant at a first pixel of the orthomosaic image based on the brightness temperature of the first pixel; and where the identified percentage of the land parcel that is covered by the first plant species is the percentage of the land parcel that is covered by the first plant species at a first time, and wherein generating a diagnostic model using the identified percentage of the land parcel that is covered by the first plant species further comprises: retrieving data indicating a second percentage of the land parcel that was covered by the first plant species at a second time before the first time, and performing a linear regression analysis on at least one of the percentage, the second percentage, the first time, and the second time to generate the diagnostic model.

Another aspect of the disclosure provides non-transitory, computer-readable storage media comprising computer-executable instructions for predicting plant growth, wherein the computer-executable instructions, when executed by a computer system, cause the computer system to: instruct an aerial vehicle to commence a flight such that the aerial vehicle captures a first set of images using a first camera; process the first set of images received from the aerial vehicle; generate an orthomosaic image using the first set of images; process the orthomosaic image to identify a percentage of a land parcel that is covered by a first plant species; generate a diagnostic model using the identified percentage of the land parcel that is covered by the first plant species; and predict future plant growth using the diagnostic model.

The non-transitory, computer-readable storage media of the preceding paragraph can include any sub-combination of the following features: where the first camera comprises a thermal imaging camera, wherein each pixel in each image in the first set corresponds to a brightness temperature, and wherein each pixel in the orthomosaic image corresponds to a brightness temperature; where the computer-executable instructions further cause the computer system to: retrieve data indicating that the first plant species is associated with a first brightness temperature, process the orthomosaic image to identify that a first set of pixels of the orthomosaic image correspond to the first brightness temperature, determine that the first set of pixels are a first percentage of a total number of pixels in the orthomosaic image, and determine that the percentage of the land parcel that is covered by the first plant species equals the first percentage; and where the identified percentage of the land parcel that is covered by the first plant species is the percentage of the land parcel that is covered by the first plant species at a first time, and wherein the computer-executable instructions further cause the computer system to: retrieve data indicating a second percentage of the land parcel that was covered by the first plant species at a second time before the first time, and perform a linear regression analysis on at least one of the percentage, the second percentage, the first time, and the second time to generate the diagnostic model.

Another aspect of the disclosure provides a system for detecting plant health. The system comprises an unmanned aerial vehicle, wherein the unmanned aerial vehicle comprises a camera. The system further comprises a computing system comprising one or more computing devices, wherein the computing system is configured to communicate with the unmanned aerial vehicle and configured with specific computer-executable instructions to: instruct the unmanned aerial vehicle to capture a first set of images using the camera while flying along a flight path; receive the first set of images from the unmanned aerial vehicle; for each image in the first set of images, convert the respective image into a plant health image; process the plant health images; and transmit a message to an external system to cause an action to be performed based on the processing of the plant health images.

The system of the preceding paragraph can include any sub-combination of the following features: where the external system comprises one of an irrigation system or a lighting system; and where the action comprises one of a lighting adjustment, a lighting schedule adjustment, a watering adjustment, a watering schedule adjustment, or a notification that plants need to be pruned.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF SPECIFIC EMBODIMENTS

Figure 1:
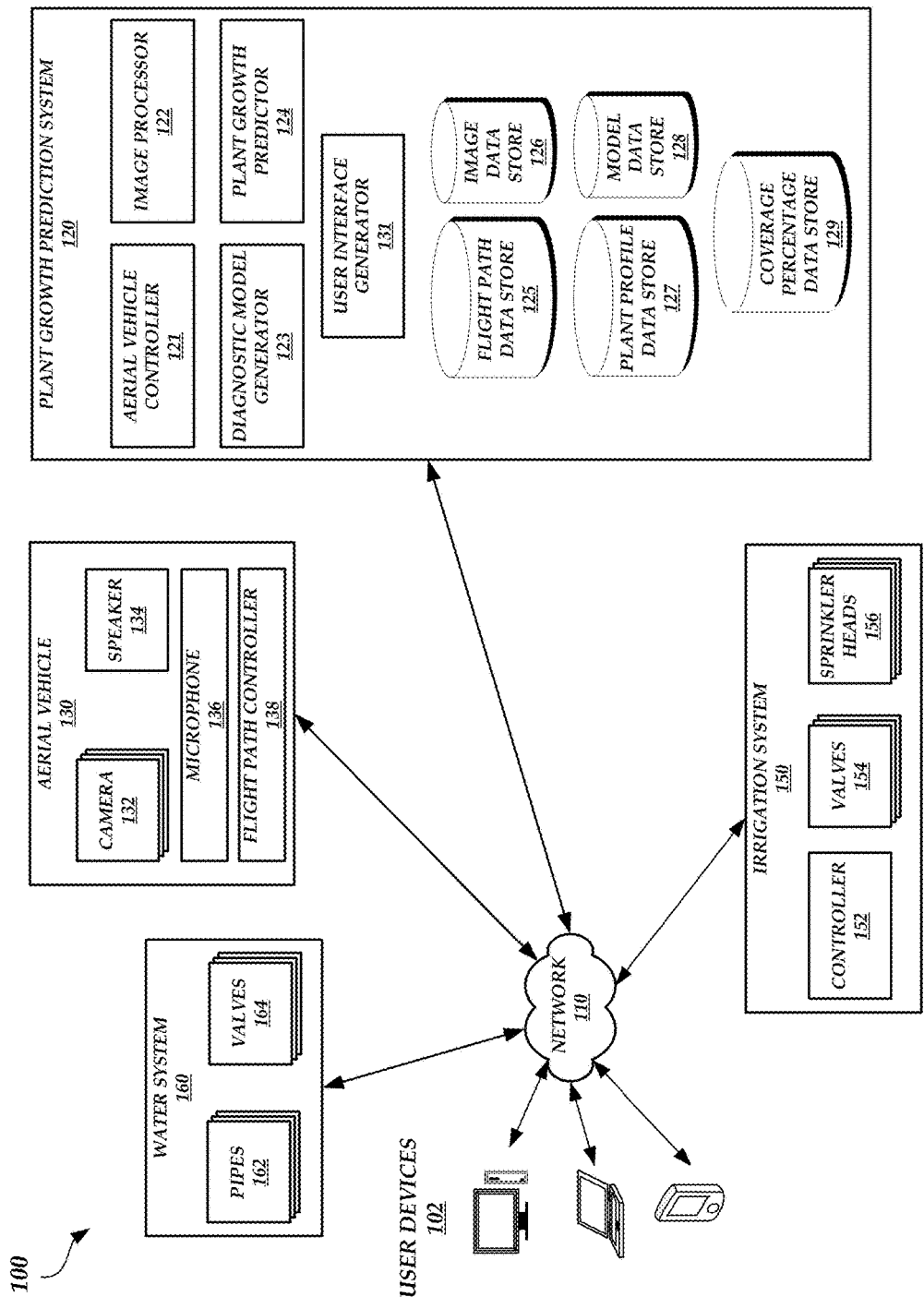
FIG. 1 is a block diagram of an illustrative operating environment in which a plant growth prediction system uses images captured by an aerial vehicle to determine current and/or predict future plant growth.

As described above, the current process of estimating plant growth at a site (e.g., a parcel or plot of land) is subjective and imprecise. For example, portions of a site may be inaccessible by a human due to the terrain, plant species that are present, and/or animal species that are present. In some cases, portions of a site may be accessed. However, if such portions are accessed, this may cause a disturbance in the site and result in inaccurate measurements and/or damage to the native vegetation and/or animal species. Thus, biologists often take samples from just a transect of the site and generate plant growth estimates based on an extrapolation of the data collected from the transect. Conventional computing systems could be used to generate plant growth estimates based on samples collected by biologists. However, these conventional computing systems do not resolve inaccuracies that may result from the samples being collected in just a transect of a site.

In particular, a biologist may analyze the collected samples to identify the plant species that were present in the transact (e.g., by visually inspecting the features of the collected samples and comparing those features to the features of known plant species, by running a DNA test and comparing the results to the DNA of known plant species, etc.) and estimate a status of the growth of a particular plant species in the entire site based on the analysis. However, a site generally will not have a uniform distribution of plant species. For example, the terrain of the site, the amount of available sunshine, the level of the water table, and/or other factors may affect whether a particular plant species will be present in a specific transect of the site. Thus, the estimation then may greatly depend on the transect from which the biologist collected samples. Given the subjectivity and variability of this estimation, it may be important to implement techniques for analyzing the plant growth across an entire site.

Accordingly, aspects of the present disclosure provide a plant growth measurement and prediction system that uses drone-captured images to measure the current growth of particular plant species and/or to predict future growth of the plant species. For example, a user, via a user device, may communicate with the plant growth prediction system to set the flight path of a drone or another aerial vehicle. The drone may be equipped with one or more cameras, such as a thermal imaging camera, a high-resolution camera (e.g., 4K, 8K, etc.), and/or the like. In an embodiment, the flight path is set such that the drone will capture images covering an entire site. Once the flight path is set, the plant growth prediction system can transmit flight path data to the drone over a network (or a wired or wireless point-to-point link) and instruct the drone to conduct a series of flights over a period of time, where each flight follows the same flight path. For example, flights may take place once ever few weeks, months, years etc. The drone may communicate with a satellite system (e.g., a global positioning system (GPS)) and/or terrestrial system to fly according to the received flight path data. As the drone flies along the provided flight path, the drone may periodically capture images of the land underneath the drone. For example, the drone can capture images directly underneath the drone (e.g., the camera(s) may be positioned such that a lens is approximately parallel with the land) and/or at an angle (e.g., the camera(s) may be positioned such that a lens deviates from being parallel with the land by a certain angle). The drone may capture images using one or more of the cameras and transmit such images to the plant growth prediction system in real-time and/or after the flight is complete.

The plant growth prediction system may stitch the received images together to form a single stitched image. For example, each image (e.g., the boundaries of the image, edges of the image, vertices of the image, individual pixels within the image, etc.) may correspond with one or more geographic coordinates (e.g., GPS coordinates). The plant growth prediction system can stitch the received images using the geographic coordinates as a guide (e.g., the plant growth prediction system can append an edge of one image to a portion of another image if the edge and portion each correspond to the same geographic coordinate or range of geographic coordinates). As described above, the flight path may be set such that the drone captures images covering an entire site. Thus, the stitched image may be an image that captures an entire site. If the drone includes different types of cameras, the plant growth prediction system can segregate images corresponding to a particular type of camera and stitch together those images that originated from a particular type of camera. Thus, the plant growth prediction system may form multiple stitched images. The plant growth prediction system can then combine the multiple stitched images to form an orthomosaic image.

As an illustrative example, if the drone captured both thermographic images (e.g., using a thermal camera) and high-resolution images (e.g., using a high-resolution camera), then the plant growth prediction system can generate a thermographic stitched image by stitching the thermographic images and a high-resolution stitched image by stitching the high-resolution images. Given that thermal cameras generally produce an image that identifies a brightness temperature of various objects captured within the image, the thermographic stitched image may then be an image that identifies the brightness temperature of various objects captured within each of the stitched thermographic images. The plant growth prediction system can then process the two stitched images by overlaying the thermographic stitched image over the high-resolution stitched image and identifying, for each pixel in the high-resolution stitched image, a brightness temperature level. The result of processing the stitched images may be an orthomosaic image.

Note that while the distribution of pixels within an image describes the spatial structure of the image, the radiometric characteristics of the pixels describe the actual content depicted in the image. For example, the sensitivity of a film or a sensor of the camera 132 to the magnitude of the electromagnetic energy present in the environment may determine the radiometric resolution of the film or sensor. The radiometric resolution of the film or sensor may describe the film or sensor's ability to discriminate very slight differences in the electromagnetic energy present in the environment. As an illustrative example, the higher the radiometric resolution of a sensor, the more sensitive the sensor is to detecting small differences in the intensity or reflectivity of the electromagnetic energy. Thus, the values of the brightness temperatures depicted within the thermographic images and the differences in brightness temperature values between different pixels may depend on the radiometric resolution of the film or sensor of the camera 132 that captured the thermographic images.

The first time a drone captures images for a particular site, the resulting orthomosaic image may be stored for future use. Once one or more additional flights take place, the plant growth prediction system can form orthomosaic images for each of these additional flights and use the orthomosaic images along with the initial orthomosaic image to identify current plant growth and/or predict future plant growth.

For example, given a known set of conditions, a plant species may radiate its kinetic temperature at a certain brightness temperature. Thus, a mapping between brightness temperature and plant species can be generated and stored in a data store. In addition, other organic and inorganic matter, such as animals, organisms other than plants and animals, dirt, water, etc., may radiate their kinetic temperature at certain brightness temperatures and mappings can be generated and stored for these types of matter as well. The plant growth prediction system can retrieve the mappings for processing each orthomosaic image. In particular, the plant growth prediction can, for each pixel in each orthomosaic image, use the mappings to identify a plant species (or animal species, other organisms, dirt, water, etc.) that maps to the brightness temperature of the respective pixel. A user, via the user device, may have specified certain plant species that are of interest. For example, in the context of habitat restoration, the user may be interested in monitoring the growth of a native plant species at a site. In addition, the user may be interested in monitoring the amount of fill present at the site (e.g., open space, dirt areas, and/or other areas that were damaged or regraded and need to be filled in), the growth of invasive species (e.g., weeds, non-native animals, and/or other objects blown in from surrounding areas), and/or plant diversity (e.g., the number of different types of plant species that are present in the site). The plant growth prediction system can then, for each orthomosaic image, use the identified plant species to determine, for a time corresponding to the respective orthomosaic image, a percentage of the site that is covered by the native species, a percentage of the site that is covered by fill, a percentage of the site that is covered by an invasive species, a count representing the plant diversity in the site, and/or the like. A percentage of a site that is covered by a particular object is referred to herein as a "coverage percentage."

Using the coverage percentages determined for a native species over a period of time, the plant growth prediction system can generate a diagnostic model. The diagnostic model can be used to predict future native species growth (e.g., represented by a coverage percentage). For example, the plant growth prediction system can perform a linear regression analysis of the coverage percentages, a cubic polynomial regression analysis of the coverage percentages, and/or the like to generate the diagnostic model. The plant growth prediction system can further generate a diagnostic model for fill, an invasive species, and/or plant diversity using the same techniques.

The diagnostic model(s) may each output a coverage percentage or plant diversity count as a function of time. Thus, the plant growth prediction system may then use the diagnostic model(s) to predict future coverage percentages and/or a plant diversity count at various times in the future. For example, the plant growth prediction system can use the diagnostic model corresponding to a native species to predict a time at which the native species will have a coverage percentage corresponding to a desired coverage percentage (e.g., a coverage percentage that indicates that the habitat restoration is complete). The plant growth prediction system can package the predictions into a report and transmit the report to a user device. In addition, the plant growth prediction system can modify one or more orthomosaic images to indicate certain information. For example, the plant growth prediction system can annotate a latest orthomosaic image to indicate areas where a native species is growing and areas in which the native species needs to grow (e.g., in fill areas) to meet a desired coverage percentage. The plant growth prediction system can also send the modified orthomosaic image(s) to the user device.

Thus, unlike the subjective estimations performed by a biologist, the techniques implemented by the plant growth prediction system described herein can result in an objective analysis of current and future plant growth. For example, a drone or other aerial vehicle can reach areas of a site that otherwise may be inaccessible or should not be accessed due to the potential damage that may be incurred. Thus, the drone can measure data for an entire site, rather than just a transect, and provide such data to the plant growth prediction system. The plant growth prediction system then can use the data for an entire site to determine an accurate representation of the current plant growth and predict future plant growth. The plant growth prediction system, therefore, determines a more accurate representation of the current plant growth and/or predicts future plant growth using techniques that previously could not even be performed by biologists.

In addition, because the drone is not necessarily capturing physical samples for later analysis (although this may occur in certain embodiments, as described below), the plant growth prediction system implements different techniques and rules than a biologist in identifying the presence of plant species for the purpose of determining current plant growth. For example, while a biologist may visit a site, retrieve physical vegetation samples, and conduct tests on the physical vegetation samples in a lab, the plant growth prediction system instead controls a drone and implements image processing techniques to identify certain characteristics of objects present in the drone-captured images (e.g., brightness temperature). Such image processing techniques include stitching images, merging stitched images, identifying the brightness temperature of a pixel in the merged image, and comparing the identified brightness temperature to plant species-brightness temperature mappings to determine a plant species that is present at the pixel. In fact, a biologist would not even be able to perform these image processing techniques (e.g., by visually inspecting the physical vegetation samples) because the brightness temperatures analyzed by the plant growth prediction system are derived from drone-captured thermal images, which are images depicting light that is invisible to humans (e.g., infrared light).

Accordingly, the plant growth prediction system described herein provides an improvement in computer-related technology (e.g., by allowing computing devices to produce more accurate determinations of current plant growth at a site and/or more accurate predictions of future plant growth at the site) using specific techniques that are not used and cannot be used by humans, who instead rely on subjective determinations in estimating current plant growth.

While the primary use case for the plant growth prediction system described herein is monitoring of habitat restoration at a site, this is merely for illustrative purposes and is not meant to be limiting. Given that organic and inorganic matter produce a certain brightness temperature under known conditions, the techniques described herein as being implemented by the plant growth prediction system can be applied to other diverse use cases. For example, the techniques described herein can be implemented for inspecting golf courses (e.g., determining current and/or predicting future plant growth), water management (e.g., the brightness temperature of soil may change as the water table rises and falls, so the techniques described herein can be used to evaluate water table levels; evaluating the surface area covered by a body of water over time for flood management purposes, for irrigation purposes, etc.; etc.), inspecting trees (e.g., determining current levels of and/or predicting future levels of the amount of cover or shade provided by trees, determining current and/or predicting future tree health given that the brightness temperature changes as trees dry out and/or die, etc.), inspect plant health (e.g., determining current levels of and/or predicting future levels of plant health given that the brightness temperature changes as plants become sick or healthier), monitoring animals (e.g., determining current and/or predicting future bird counts, determining current and/or predicting future endangered species counts, etc.), monitoring invasive species (e.g., determining current and/or predicting future weed growth), mapping fire fuel (e.g., determining current and/or predicting future growth of plants susceptible to extending the life of a fire), inspecting erosion (e.g., different soil layers may correspond to different brightness temperatures, so the movement or appearance of soil layers over time can be determined and/or predicted), evaluating common areas (e.g., for a homeowners association or park to determine and/or predict plant growth), inspecting mining operations (e.g., determining current and/or predicting future water movement, determining current and/or predicting future growth of reintroduced plants, etc.), landscaping (e.g., determining current and/or predicting future plant growth), monitoring a waste reclamation site (determining current and/or predicting future plant growth), monitoring vineyards (e.g., determining current and/or predicting future grapevine growth, determining current and/or predicting future invasive plant and/or animal species growth, etc.), monitoring nurseries (determining current and/or predicting future plant growth), and/or for any other use cases in which it may be beneficial to measure and/or predict plant growth.

The foregoing aspects and many of the attendant advantages of this disclosure will become more readily appreciated as the same become better understood by reference to the following detailed description, when taken in conjunction with the accompanying drawings.

Example Plant Growth Prediction Environment

FIG. 1 is a block diagram of an illustrative operating environment 100 in which a plant growth prediction system 120 uses images captured by an aerial vehicle 130 to determine current plant growth and/or predict future plant growth. The operating environment 100 further includes various user devices 102 that may communicate with the plant growth prediction system 120 via a network 110 to provide flight path parameters, to receive generated reports, and/or to receive modified images indicating current and/or predicted plant growth. In addition, the operating environment 100 may further include an irrigation system 150 and a water system 160 that can be controlled directly or indirectly by the plant growth prediction system 120.

The aerial vehicle 130 may be an unmanned aerial vehicle. For example, the aerial vehicle 130 may be four or six rotor drone. Alternatively, the aerial vehicle 130 can be a manned aerial vehicle. In some embodiments, two or more unmanned aerial vehicles may be used concurrently at a given site to perform the functionality described herein with respect to a single aerial vehicle 130. The aerial vehicle 130 may include one or more cameras 132. For example, each camera 132 may be a different type of camera, such as a thermal imaging camera, a high-resolution camera (e.g., 4K, 8K, etc.), and/or the like. Alternatively or in addition, one camera 132 may include multiple lenses such that the camera 132 can capture different types of images. The camera(s) 132 may be mounted to a bottom and/or side surface of the aerial vehicle 130 such that the camera(s) 132 can capture images of the land underneath the aerial vehicle 130. In some embodiments, one or more of the cameras 132 are mounted to a gimbal that mounts to a bottom and/or side surface of the aerial vehicle 130 to allow for camera 132 rotation. One or more of the cameras 132 may include a network interface (e.g., a universal serial bus (USB) port, an Ethernet port, a wireless transceiver, etc.) to communicate with the plant growth prediction system 120 via the network 110 (or via a wired or wireless point-to-point link). Alternatively, the cameras 132 may transmit data (e.g., captured images) to a network interface (e.g., a universal serial bus (USB) port, an Ethernet port, a wireless transceiver, etc., not shown) of the aerial vehicle 130 for eventual transmission to the plant growth prediction system 120.

The aerial vehicle 130 may further include a flight path controller 138. The flight path controller 138 may communicate with the plant growth prediction system 120 to receive flight path parameters. For example, flight path parameters may include a flight path (e.g., one or more geographic coordinates, waypoints, flight length, flight time, speed, altitude, flight course mode, a front overlap ratio (e.g., a front overlap of the defined boundaries of a capture site that is necessary for the one or more cameras 132 to fully capture the capture site, represented as a percentage), a side overlap ratio (e.g., a side overlap of the defined boundaries of a capture site that is necessary for the one or more cameras 132 to fully capture the capture site, represented as a percentage), a course angle, etc.), a shooting angle (e.g., an angle at which one or more cameras 132 is positioned to capture images), a capture mode (e.g., a setting indicating when the one or more cameras 132 capture images), a gimbal pitch angle (e.g., an angle of a lens of the one or more cameras 132), an end-mission action (e.g., hover, return to start, etc.), camera resolution, and/or the like. Alternatively, the flight path controller 138 can communicate directly with a user device 102, such as a user device 102 present at a site with the aerial vehicle 130.

Upon receiving flight path parameters, the flight path controller 138 can control the operation of the aerial vehicle 130 according to the flight path parameters. For example, the flight path controller 138 can transmit instructions to various components of the aerial vehicle 130 to cause the aerial vehicle 130 to take off from a current location, follow a certain flight path, instruct the camera(s) 132 to capture images at the appropriate time and at the appropriate angle, and land once the flight is complete. Commercially available drones, such as the DJI PHANTOM 3 or INSPIRE 1 PRO unmanned aerial vehicles, and associated code (e.g., such as the live view application provided with the DJI PHANTOM 3 unmanned aerial vehicle) may provide such features. In some embodiments, the plant growth prediction system 120 can transmit updated flight path parameters to the flight path controller 138 while the aerial vehicle 130 is in flight. When updated flight path parameters are received in flight, the flight path controller 138 can transmit instructions to various components of the aerial vehicle 130 to cause the aerial vehicle 130 to adjust flight according to the updated flight path parameters.

The flight path controller 138 may further include instructions that, when executed, cause the aerial vehicle 130 to deviate from the selected flight path at the instruction of a user and/or automatically. For example, as described below, the aerial vehicle 130 can transmit captured images in real-time (e.g., as the images are captured) to the plant growth prediction system 120. The plant growth prediction system 120 (e.g., the image processor 122 described below) may provide one or more user devices 102 with access to the captured images as they are received during a flight. For example, the plant growth prediction system 120 (e.g., the user interface generator 131 described below) may generate user interface data that is transmitted to a user device 102 and that causes the user device 102 to display a user interface showing the images as the images are captured by the one or more cameras 132. A user viewing the user interface and captured images may notice an object of interest and can use controls provided by the user interface to transmit instructions to the aerial vehicle 130 via the plant growth prediction system 120 that causes the aerial vehicle 130 to return to the location where the object of interest was noticed. As another example, the plant growth prediction system 120 (e.g., the image processor 122) and/or the flight path controller 138 can be configured to process captured images as the camera(s) 132 captures such images to identify certain objects and, if such objects are identified, instruct the aerial vehicle 130 or otherwise cause the aerial vehicle 130 to deviate from the flight path to revisit the identified object (e.g., to capture additional images). The plant growth prediction system 120 and/or flight path controller 138 can use data indicating the shape and/or brightness temperature of specific objects to process a captured image and determine whether an object with the same shape and/or brightness temperature is present. Note that the flight path controller 138 may intercept and/or receive images captured by the camera(s) 132 in order to perform the processing.

Optionally, the aerial vehicle 130 includes a speaker 134 and/or microphone 136. For example, the aerial vehicle 130 may be instructed to capture images for the purpose of monitoring an animal population (e.g., birds, rodents, deer, endangered species, etc.). The speaker 134 may output a sound that resembles a sound produced by the subject animal species (e.g., a bird call). The microphone 136 may be enabled to listen for sounds that are produced in response to the sound output by the speaker 134. The aerial vehicle 130 can transmit the sounds picked up by the microphone 136 along with the geographic coordinates at which the sounds were received to the plant growth prediction system 120 for analysis. In particular, the plant growth prediction system 120 may store a mapping of sounds to specific animal species. Thus, the plant growth prediction system 120 can process the received sounds to identify whether the sounds resemble sounds associated with a known animal species. If a match occurs, then the plant growth prediction system 120 can determine that at least one animal of the animal species was present in the vicinity of a location at which the sound was picked up by the microphone 136. This audio processing can supplement the image processing described herein to provide a more accurate determination of a current animal population and/or a more accurate prediction of a future animal population. In addition, the audio data may help the plant growth prediction system 120 provide accurate determinations of a current animal population and/or accurate predictions of a future animal population even if the particular animal species is not visible in the captured images.

In further embodiments, not shown, the aerial vehicle 130 includes a mechanical and/or pneumatic attachment (e.g., a mechanical and/or pneumatic arm) configured to obtain and hold items, collect samples, and/or the like. During flight, the aerial vehicle 130 can use the mechanical attachment to perform such actions and record, using the current geographic coordinates of the aerial vehicle 130, a location at which such actions were performed. The location information may then be used in determining current and/or predicted plant growth and/or for modifying an orthomosaic image to indicate a location where an action was performed.

In further embodiments, the aerial vehicle 130 may include sensors, not shown, to perform obstacle avoidance. For example, the aerial vehicle 130 may be flying at a low altitude (e.g., 8-9 meters). Tree branches, terrain, and/or other objects may therefore impede the flight path of the aerial vehicle 130. The aerial vehicles 130 (e.g., the flight path controller 138) can therefore use the sensors to detect objects to the front and/or side of the aerial vehicle 130, adjust a flight path of the aerial vehicle 130 to avoid the detected objects, and then return to the flight path set by the flight path parameters once the aerial vehicle 130 is clear of the detected objects.

The plant growth prediction system 120 can be a computing system configured to periodically instruct the aerial vehicle 130 to capture images along a flight path above a site and use the captured images to determine current plant growth and/or predict future plant growth at the site. For example, the plant growth prediction system 120 may be a single computing device, or it may include multiple distinct computing devices, such as computer servers, logically or physically grouped together to collectively operate as a server system, or independent components or devices that are or are not networked together, but that are used in combination to perform the operations described herein. As an illustrative example, one computing device in the plant growth prediction system 120 may perform the operations described below with respect to aerial vehicle controller 121, while another, separate computing device in the plant growth prediction system 120 may perform the operations described below with respect to the plant growth predictor 124. The components of the plant growth prediction system 120 can each be implemented in application-specific hardware (e.g., a server computing device with one or more ASICs) such that no software is necessary, or as a combination of hardware and software. In addition, the modules and components of the plant growth prediction system 120 can be combined on one server computing device or separated individually or into groups on several server computing devices. In some embodiments, the plant growth prediction system 120 may include additional or fewer components than illustrated in FIG. 1.

In some embodiments, the features and services provided by the plant growth prediction system 120 may be implemented as web services consumable via the communication network 110. In further embodiments, the plant growth prediction system 120 is provided by one more virtual machines implemented in a hosted computing environment. The hosted computing environment may include one or more rapidly provisioned and released computing resources, which computing resources may include computing, networking and/or storage devices. A hosted computing environment may also be referred to as a cloud computing environment.

The plant growth prediction system 120 may include various modules, components, data stores, and/or the like to provide the plant growth measurement and prediction functionality described herein. For example, the plant growth prediction system 120 may include an aerial vehicle controller 121, an image processor 122, a diagnostic model generator 123, a plant growth predictor 124, a flight path data store 125, an image data store 126, a plant profile data store 127, a model data store 128, a coverage percentage data store 129, and a user interface generator 131.

The aerial vehicle controller 121 may receive flight path parameters from the user device 102 via the network 110. In an embodiment, the user device 102 sets the flight path such that the aerial vehicle 130 captures images covering an entire site. As described in greater detail below with respect to FIGS. 5A-5B, the user device 102 may present a user interface that allows a user to visually set the flight path and one or more flight path parameters. The user device 102 may additional provide the aerial vehicle controller 121 with a set of times or phases at which the aerial vehicle 130 should conduct flights. For example, the user device 102 may indicate that a first flight should occur before any impact to the site has occurred, a second flight should occur once impact to the site has commenced (e.g., a portion of the site is under construction, plant material has been removed, surface lines have been installed, trenches have been dug, etc.), a third flight should occur once plants are being installed, a fourth flight should occur as plant material begins to mature, and/or any times after the plant material has begun to mature. Time intervals between flights may be in the minutes, hours, days, weeks, months, years, etc. In an embodiment, the aerial vehicle controller 121 stores the flight path parameters in the flight path data store 125 in an entry associated with the site such that the flight path parameters can be retrieved and reused for each subsequent flight (e.g., each flight may occur according to the same flight path parameters).

Once the aerial vehicle controller 121 determines that the aerial vehicle 130 should conduct a flight at a current time, a project member may bring the aerial vehicle 130 to the site (e.g., based on a reminder provided by the plant growth prediction system 120). The aerial vehicle controller 121 can transmit the flight path parameters to the aerial vehicle 130 over the network 110 and instruct the aerial vehicle 130 (e.g., the flight path controller 138) to begin the flight. The aerial vehicle 130 (e.g., the flight path controller 138) may communicate with a satellite system (e.g., a GPS system) and/or terrestrial system to fly according to the received flight path parameters. As the aerial vehicle 130 travels along the indicated flight path, the aerial vehicle 130 captures images of the land underneath the aerial vehicle 130 at an interval determined by the capture mode and in a manner determined by the shooting angle and/or the gimbal pitch angle using the one or more cameras 132. For example, the one or more cameras 132 can capture images directly underneath the aerial vehicle 130 (e.g., the camera(s) 132 may be positioned such that a lens is approximately parallel with the land, facing straight down) and/or at an angle (e.g., the camera(s) 132 may be positioned such that a lens deviates from being parallel with the land by a certain angle). The camera(s) 132 and/or a network interface (not shown) may transmit captured images to the image processor 122 in real-time (e.g., as the images are captured) and/or after the flight is complete.

The image processor 122 may stitch the received images together to form a single stitched image. For example, the aerial vehicle 130 may transmit metadata associated with each image. The metadata may indicate portions of the image (e.g., the boundaries of the image, edges of the image, vertices of the image, individual pixels within the image, etc.) that correspond to particular geographic coordinates (e.g., as determined by the aerial vehicle 130 via communications with the GPS system). The image processor 122 can stitch the received images using the geographic coordinates provided in the metadata as a guide. For example, the image processor 122 can append an edge of one image to an edge of another image if the edges each correspond to the same geographic coordinate or range of geographic coordinates. As another example, the image processor 122 can append an edge of one image to a portion of another image if the edge and portion each correspond to the same geographic coordinate or range of geographic coordinates. As described above, the flight path may be set such that the aerial vehicle 130 captures images covering an entire site. Thus, the stitched image may be an image that captures an entire site.

If the aerial vehicle 130 includes different types of cameras 132, then the image processor 122 can segregate images corresponding to a particular type of camera 132 and stitch together those images that originated from a particular type of camera 132. Thus, the image processor 132 may form multiple stitched images. The image processor 122 can then combine the multiple stitched images to form an orthomosaic image. For example, the image processor 122 may use a digital elevation model (DEM) of the site to combine the multiple stitched images using orthorectification techniques such that the stitched images are geometrically corrected to have a uniform scale. In other words, the image processor 122 may form an orthomosaic image that has the same lack of distortion as a map and can be used to measure true distances.

As an illustrative example, if the aerial vehicle 130 captures both thermographic images (e.g., using a thermal camera 132) and high-resolution images (e.g., using a high-resolution camera 132), then the image processor 122 can generate a thermographic stitched image by stitching the thermographic images and a high-resolution stitched image by stitching the high-resolution images. Given that thermal cameras 132 generally produce an image that identifies a brightness temperature of various objects captured within the image, the thermographic stitched image may then be an image that identifies the brightness temperature of various objects captured within each of the stitched thermographic images. The image processor 122 can then process the two stitched images by overlaying the thermographic stitched image over the high-resolution stitched image and identifying, for each pixel in the high-resolution stitched image, a brightness temperature level. The result of processing the stitched images may be an orthomosaic image.

Given that different objects have different emissivity levels, the image processor 122 may adjust an emissivity sensitivity level of one or more of the thermographic images before the stitching is performed depending on the type of prediction that the plant growth prediction system 120 will eventually perform. For example, plant material may have high emissivity levels (e.g., between 0.94 and 0.96), whereas water may have lower emissivity levels (e.g., around 0.67). Thus, as an illustrative example, the image processor 122 may adjust the emissivity sensitivity level of the thermographic images to between 0.94 and 0.96 if determining current and/or predicting future plant growth and may adjust the emissivity sensitivity level of the thermographic images to around 0.67 if determining current and/or predicting future water table levels.

The pixels in an orthomosaic image may be labeled, shaded (e.g., with specific colors that indicate brightness temperature), or otherwise annotated to indicate the identified brightness temperature levels. Such labels, shading, or annotations may be visible or invisible when a device, such as the user device 102, displays the orthomosaic image. For example, a background of the orthomosaic image may be the geometrically-corrected high-resolution stitched image. The pixels of the orthomosaic image may then be shaded colors corresponding to the identified brightness temperature of the respective pixels. Alternatively, the orthomosaic image may be associated with metadata that identifies the brightness temperature levels of each pixel in the orthomosaic image.

The image processor 122 may store the orthomosaic image generated from images captured during a flight in the image data store 126. If a stored orthomosaic image corresponds to a first flight for a particular site, the plant growth prediction system 120 may take no further action. However, once one or more additional flights take place and the image processor 122 forms one or more additional orthomosaic images, the plant growth prediction system 120 can use the stored orthomosaic images to identify current plant growth and/or predict future plant growth at the site.

For example, given a known set of conditions, a plant species may radiate its kinetic temperature at a certain brightness temperature. Thus, mappings between brightness temperature and plant species can be generated and stored in the plant profile data store 127. In addition, other organic and inorganic matter, such as animals, organisms other than plants and animals, dirt, water, etc., may radiate their kinetic temperature at certain brightness temperatures and mappings can be generated and stored in the plant profile data store 127 for these types of matter as well.

In further embodiments, leaf, plant, and/or animal shape (e.g., detected via a pattern recognition process implemented by the image processor 122); leaf, plant, and/or animal color; leaf, plant, and/or animal size; and/or the like may be mapped to particular plant and/or animal species. Such mappings can also be stored in the plant profile data store 127 for use by the image processor 122 identifying plant and/or animal species.

The image processor 122 can retrieve one or more mappings from the plant profile data store 127 for individually processing each orthomosaic image. In particular, the image processor 122 can, for each pixel in each orthomosaic image, use the mappings to identify a plant species (or animal species, other organisms, dirt, water, etc.) that maps to the brightness temperature of the respective pixel.

Optionally, the image processor 122 can, for some or all of the pixels in each orthomosaic image, use the mappings to identify individual plants (or animals, other organisms, dirt, water, etc.). For example, a user, via the user device 102, may view one or more of the orthomosaic images and define one or more transects corresponding to the area of land depicted in the one or more orthomosaic images (e.g., in the habitat or site). The user can identify a number of transects that should be included in the area of land depicted in the one or more orthomosaic images, the shape of each of these transects, and/or a direction of the transects (e.g., if the habitat is along a coastline, the transect may begin at the coastline and the direction of the transect may be a certain distance inland from the coastline). The image processor 122 can then, for some or all of the pixels in each orthomosaic image that falls within a transect, use the mappings to identify a plant species (or animal species, other organisms, dirt, water, etc.) that maps to the brightness temperature of the respective pixel (e.g., to determine that the respective pixel corresponds to a plant species rather than other material). The image processor 122 can then identify the plant (or animal, other organism, dirt, water, etc.) at the respective pixel as a separate, individual plant of the identified plant species (or animal species, other organisms, dirt, water, etc.). Upon identifying individual plants (or animals, other organisms, dirt, water, etc.), the image processor 122 may annotate or label the corresponding pixel(s) (e.g., place a pinpoint at the corresponding pixel) such that the user can identify, within a user interface, individual plants (or animals, other organisms, dirt, water, etc.) and track the individual plants' growth (or lack of growth) over time (e.g., by viewing different orthomosaic images). Because portions of the orthomosaic images correspond to particular geographic coordinates, each individual plant (or animal, other organism, dirt, water, etc.) can be associated with geographic coordinates, a volume of the respective individual plant (or animal, other organism, dirt, water, etc.), a height of the respective individual plant (or animal, other organism, dirt, water, etc.), a width of the respective individual plant (or animal, other organism, dirt, water, etc.), and/or the like. The geographic coordinates, volume, height, width, and/or the like for individual plants (or animals, other organisms, dirt, water, etc.) can be stored in a data store of the plant growth prediction system 120 (e.g., the coverage percentage data store 129). The user interface generator 131 can retrieve this information to, for example, generate user interface data that, when rendered by the user device 102, causes the user device 102 to display the historical growth of one or more individual plants (or animals, other organisms, dirt, water, etc.).

A user, via the user device 102, may have provided the image processor 122 with a list of plant species that are of interest and/or a list of plant species that are not of interest. For example, in the context of habitat restoration, the user device 102 may transmit to the image processor 122 a list identifying one or more native plant species, fill (e.g., open space, dirt areas, and/or other areas that were damaged or regraded and need to be filled in), one or more invasive species (e.g., weeds, non-native animals, and/or other objects blown in from surrounding areas), and/or plant diversity (e.g., the number of different types of plant species that are present in the site) as items to monitor. Optionally, the user device 102 transmits to the image processor 122 a list of species to ignore. Thus, the image processor 122 can then, for each orthomosaic image, use the identified plant species (or animal species, other organisms, dirt, water, etc.) to determine a percentage of the site that is covered by the native species, a percentage of the site that is covered by fill, a percentage of the site that is covered by an invasive species, a count representing the plant diversity in the site, and/or the like. Because each orthomosaic image is associated with a flight that occurred at a particular time, the image processor 122 can associate the determined coverage percentages and/or plant diversity with the time (e.g., day) that the corresponding flight took place. The image processor 122 can store the determined coverage percentages and/or plant diversity in the coverage percentage data store 129 in an entry associated with the associated time and the site.

In further embodiments, the image processor 122 can use deduplication techniques to reduce the likelihood that a plant is double-counted when determining the coverage percentages. For example, the image processor 122 can use the geographic coordinates included within the metadata associated with an image taken during a first flight to establish a location of a plant. As an illustrative example, each pixel in the image may map to a set of geographic coordinates according to the metadata. The image processor 1222 can then map each pixel in the orthomosaic image to a set of geographic coordinates. The image processor 122 may then identify a plant species in a manner as described herein, where the image processor 122 maps a pixel to a plant species. Because the pixel also maps to a set of geographic coordinates, the image processor 122 can map the set of geographic coordinates to the plant species. When processing a new orthomosaic image generated as a result of an additional flight, the image processor 122 repeat the same process to identify a plant species location and determine a geographic coordinate-to-plant species mapping. Thus, by repeating the process, the image processor 122 can avoid double-counting a plant when determining the coverage percentages.

In further embodiments, the image processor 122 can implement techniques to remove objects from a generated orthomosaic image. For example, the image processor 122 may be instructed to ignore certain plant and/or animal species. Using the mappings stored in the plant profile data store 127, the image processor 122 can identify pixels that correspond to a plant or animal species to ignore and, for example, remove any labels, shading, or annotations that indicates a brightness temperature of those pixels.

While the aerial vehicle controller 121 and the image processor 122 are depicted as being located internal to the plant growth prediction system 120, this is not meant to be limiting. For example, the aerial vehicle controller 121 and/or the image processor 122 (or a component that implements at least a portion of the image processor 122 functionality described herein) may be internal to another computing device present at the site where the aerial vehicle 130 is located. Alternatively, the plant growth prediction system 120 (or one or more components of the plant growth prediction system 120) may itself be present at the site where the aerial vehicle 130 is located.

The diagnostic model generator 123 may then retrieve the native species coverage percentages of a site stored in the coverage percentage data store 129. For example, the diagnostic model generator 123 can retrieve the native species coverage percentages once the image processor 122 has determined the values, when a user device 102 transmits a request for a status report of the site (e.g., current plant growth levels and/or predicted future plant growth levels), when the plant growth prediction system 120 has a low CPU usage (e.g., less than 50%), etc. Using the retrieved native species coverage percentages, the diagnostic model generator 123 can generate a diagnostic model. The diagnostic model can be used to predict future native species growth (e.g., represented by a coverage percentage). For example, the diagnostic model generator 123 can perform a linear regression analysis of the native species coverage percentages, a cubic polynomial regression analysis of the native species coverage percentages, and/or the like to generate the diagnostic model.

As an illustrative example, the diagnostic model generator 123 may calculate an average of the native species coverage percentages and an average of the times associated with the native species coverage percentages. The diagnostic model generator 123 may define the linear regression as follows:

$$A = \bar{y} - B\bar{k} \quad (1)$$

where $\bar{y}$ represents an average percentage coverage, $\bar{x}$ represents an average time, and B is defined as follows:

$$B = \frac{S_{xy}}{S_{xx}} \quad (2)$$

where $S_{xx}$ is defined as follows:

$$S_{xx} = \frac{\sum x_t^2}{n} - \bar{x}^2 \quad (3)$$

and where $S_{xy}$ is defined as follows:

$$S_{xy} = \frac{\sum x_t y_t}{n} - \overline{xy} \quad (4)$$

The diagnostic model generator 123 can apply Equations (1) through (4) using the calculated average native species coverage percentages and the calculated average times to generate a linear regression diagnostic model.

The diagnostic model generator 123 can further generate a diagnostic model for fill, an invasive species, and/or plant diversity using the same techniques. The diagnostic model generator 123 can then store the diagnostic models in the model data store 128 in an entry associated with the site.

The diagnostic model(s) may each output a coverage percentage or plant diversity count as a function of time. Thus, the plant growth predictor 124 may then retrieve one or more diagnostic models corresponding to the site from the model data store 128 and use the diagnostic model(s) to predict future coverage percentages and/or a plant diversity count at various times in the future. For example, the plant growth predictor 124 can use the diagnostic model corresponding to a native species to predict a time at which the native species will have a coverage percentage corresponding to a desired coverage percentage (e.g., a coverage percentage that indicates that the habitat restoration is complete). As an illustrative example, the plant growth predictor 124 can identify a time value that corresponds with a value of the desired coverage percentage that falls along a trend line of the native species diagnostic model. Alternatively or in addition, the plant growth predictor 124 can use the native species diagnostic model to determine a predicted coverage percentage at set times in the future (e.g., 1 year from a current date, 5 years from a current date, etc.).

The plant growth predictor 124 can package the coverage percentage and/or plant diversity predictions (along with historical and/or current coverage percentages and/or plant diversity numbers) into a report and transmit the report to a user device 102 (e.g., either the same user device 102 that provided the flight path parameters or a different user device 102). The plant growth predictor 124 can transmit the report at the request of the user device 102.

In addition, the plant growth predictor 124 can modify one or more orthomosaic images to indicate certain information. For example, the plant growth indicator 124 can annotate a most-recent orthomosaic image to indicate areas where a native species is growing and areas in which the native species needs to grow (e.g., in fill areas) to meet a desired coverage percentage. As an illustrative example, the plant growth indicator 124 can retrieve current coverage percentages from the coverage percentage data store 129. The plant growth indicator 124 can then determine a difference between the current native species coverage percentage and a desired native species coverage percentage to identify a diagnostic variance (e.g., represented as a percentage). Thus, the diagnostic variance may represent a percentage of the site that needs to be filled with the native species to meet the desired native species coverage percentage. The plant growth indicator 124 can annotate a portion of the orthomosaic image corresponding to fill areas and/or invasive species that is a percentage of the site equal to the diagnostic variance, thereby indicating that the annotated portion needs to be filled with the native species instead to meet the desired native species coverage percentage. The plant growth indicator 124 can also transmit the modified orthomosaic image(s) to the user device 102.

Figure 5A:
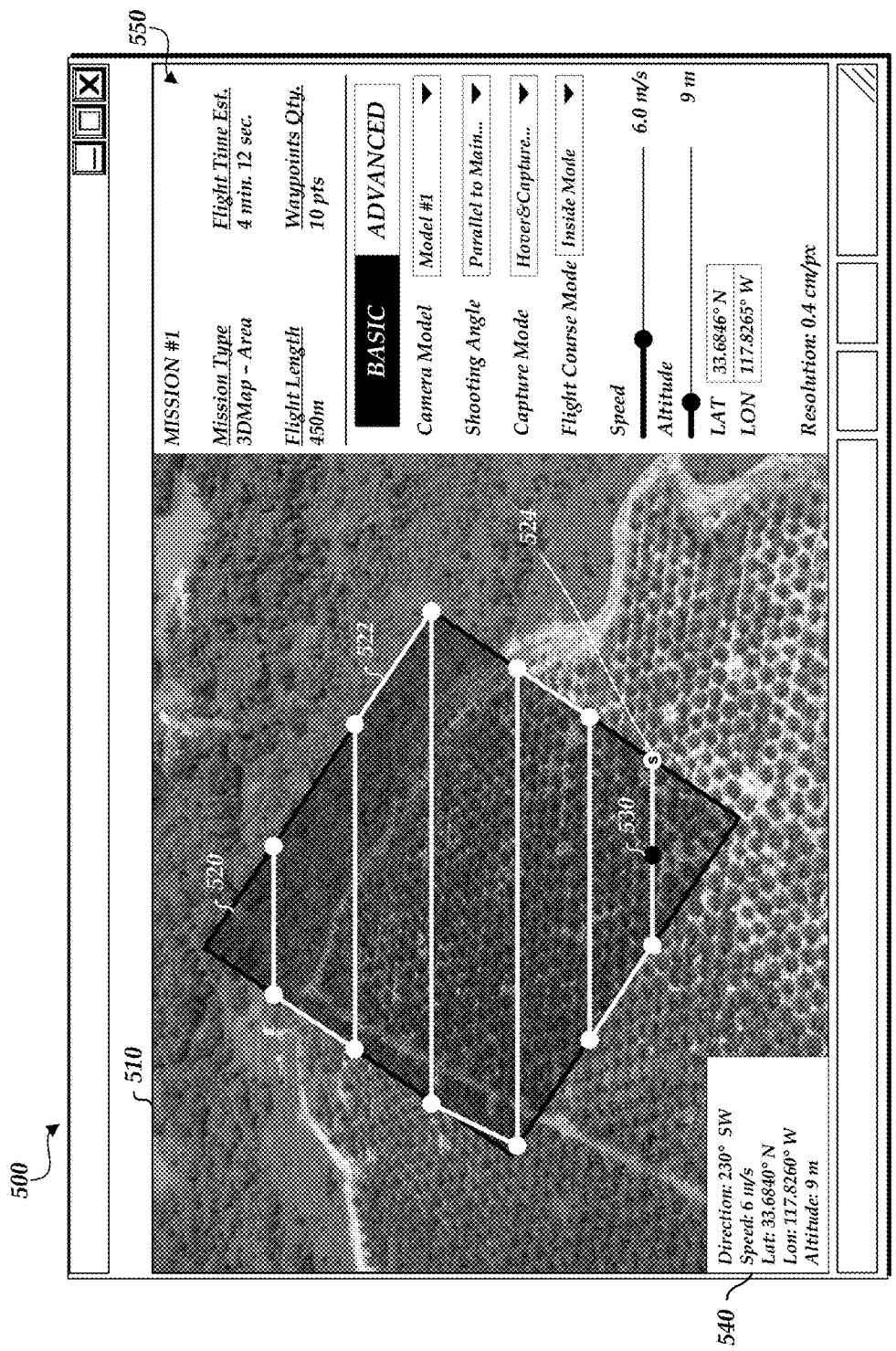
FIG. 5A illustrates a user interface displaying a site and a list of basic flight path parameters.
Figure 5B:
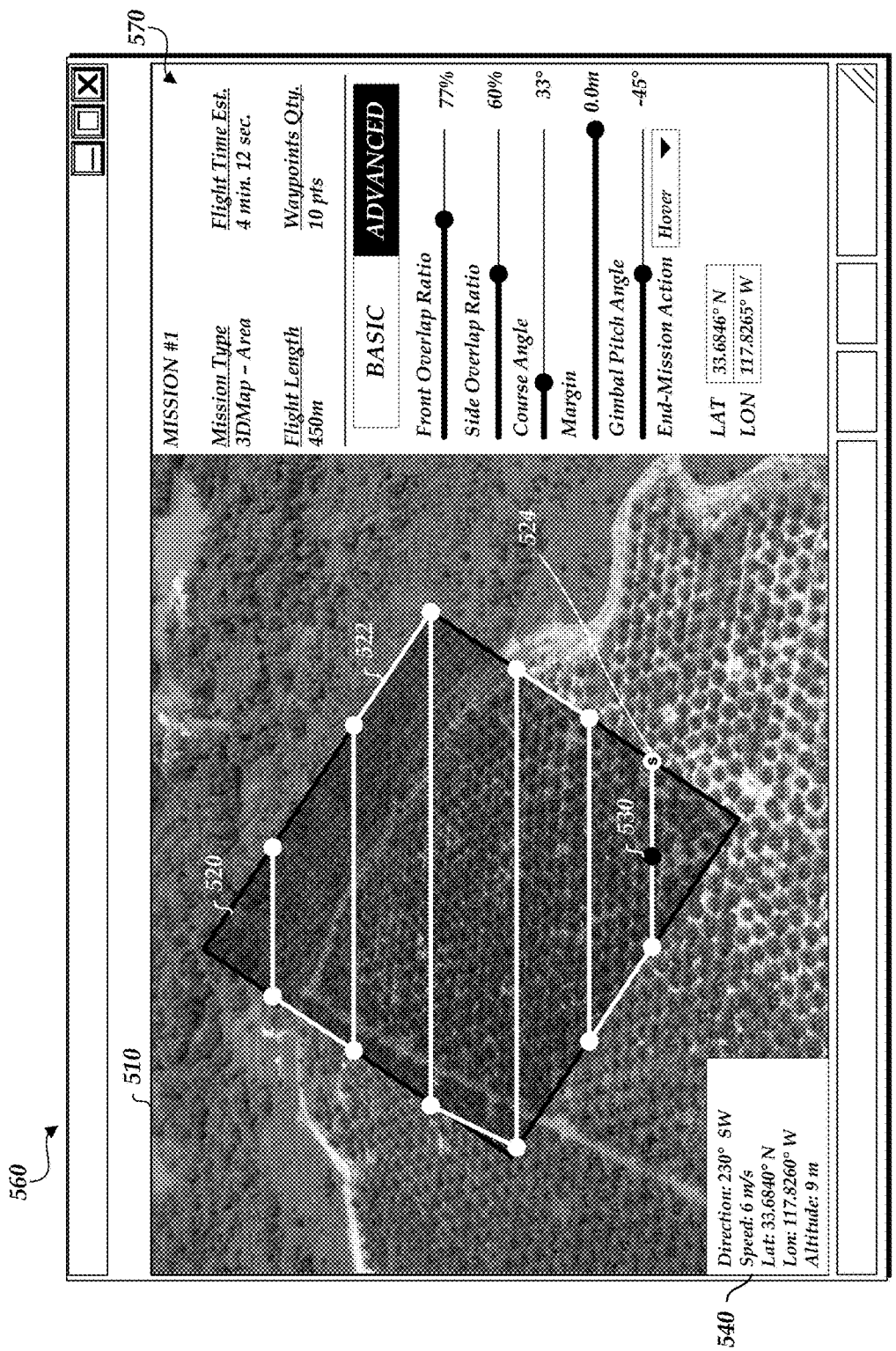
FIG. 5B illustrates a user interface displaying the site and a list of advanced flight path parameters.

The user interface generator 131 can generate user interface data and transmit the user interface data to a user device 102. The user interface data, when rendered by the user device 102, may cause the user device to display a site, navigation controls for controlling the flight of the aerial vehicle 130, and/or other selectable flight path parameters. Example user interfaces that may be displayed by the user device 102 based on the user interface data generated by the user interface generator 131 are depicted in FIGS. 5A-5B.

In further embodiments, the plant growth prediction system 120 may be instructed to determine current levels and/or predict future levels for two or more different types of objects. For example, the plant growth prediction system 120 may be instructed to determine current and/or predict future growth of a first plant species and may be instructed to determine current and/or predict future counts of a first bird species. It may be that the ideal altitude to measure such information may be different for each type of object. Thus, the user device 102 may provide flight path parameters that indicate two different altitudes for the same flight path. Thus, upon receiving instructions from the aerial vehicle controller 121, the aerial vehicle 130 may fly along the flight path at the lower altitude in a first pass and then fly along the flight path at the higher altitude in a second pass, or vice-versa. While the first pass may be for measuring levels for a first object, the image processor 122, the diagnostic model generator 123, and/or the plant growth predictor 124 may nonetheless use images captured at each altitude in order to form the orthomosaic image, generate the diagnostic model(s) and/or generate predictions, respectively.

In further embodiments, the plant growth prediction system 120 can control operation of the water system 160. For example, the water system 160 may be the water system for a municipality, state, or other geographic region. The water system 160 may include one or more pipes 162 that are controlled by one or more valves 164. The image processor 122 can process an orthomosaic images and/or a thermographic image to identify underground and/or above ground leaks originating from one or more of the pipes 162. As described herein, the thermographic image capture light, such as infrared light, invisible to humans. Thus, the thermographic image (and therefore the orthomosaic image) may depict objects present below the surface or other objects that are otherwise invisible to humans. In one example, such objects can include the flow of water below a sidewalk, below the pavement, and/or the like, that result from a leak or water main break. The image processor 122 may identify the flow of water based on comparing the shape and/or color of the pixels present in the thermographic or orthomosaic image with known shapes and/or colors of water (e.g., the shape may be a thin and snake-like, similar to a stream or river, and the color may be within the blue color spectrum or any other color representing the wavelength of light emitted by water). The image processor 122 may further recognize one or more pipes 162 in the thermographic or orthomosaic image (e.g., based on comparing objects in the image to known shapes and/or colors of pipes 162), thereby allowing the image processor 122 to identify the specific pipe 162 from which the water is flowing. Once the image processor 122 identifies the pipe 162 from which the water is flowing, the image processor 122 can generate and transmit a message to a valve 164 corresponding to the identified pipe 162 via the network 110, where receipt of the message causes the valve 164 to shut off the flow of water through the pipe 162. Accordingly, the plant growth prediction system 120 can automatically detect a leak and transmit instructions to cause the flow of water to stop such that the leak can be fixed.

The flight path data store 125 stores flight path parameters for various sites. While the flight path data store 125 is depicted as being located internal to the plant growth prediction system 120, this is not meant to be limiting. For example, not shown, the flight path data store 125 can be located external to the plant growth prediction system 120.

The image data store 126 stores images captured by the aerial vehicle 130 and/or orthomosaic images generated by the image processor 122. The images may be stored in entries associated with a site and a time and/or flight identification identifying when the images were captured. While the image data store 126 is depicted as being located internal to the plant growth prediction system 120, this is not meant to be limiting. For example, not shown, the image data store 126 can be located external to the plant growth prediction system 120.

The plant profile data store 127 stores mappings of plant species to brightness temperatures. The plant profile data store 127 may also store mappings of other organic and inorganic matter, such as animals, organisms other than plants and animals, dirt, water, etc., to brightness temperatures. The plant profile data store 127 may further store emissivity levels for various plant species, animal species, organisms other than plants and animals, dirt, water, etc. such that the emissivity levels could be used by the image processor 122 to adjust the emissivity sensitivity levels of captured thermographic images. While the plant profile data store 127 is depicted as being located internal to the plant growth prediction system 120, this is not meant to be limiting. For example, not shown, the plant profile data store 127 can be located external to the plant growth prediction system 120.

The model data store 128 stores diagnostic models generated by the diagnostic model generator 123. Each diagnostic model may be stored in an entry associated with a site. While the model data store 128 is depicted as being located internal to the plant growth prediction system 120, this is not meant to be limiting. For example, not shown, the model data store 128 can be located external to the plant growth prediction system 120.

The coverage percentage data store 129 stores coverage percentages and/or plant diversity determined by the image processor 122. The coverage percentages may be stored in entries associated with a site and a time. Optionally, the coverage percentage data store 129 may also store plant material data, such as the geographic coordinates, volume, height, width, and/or the like of individual plants. The plant material data may be stored in entries associate with a site and/or time. While the coverage percentage data store 129 is depicted as being located internal to the plant growth prediction system 120, this is not meant to be limiting. For example, not shown, the coverage percentage data store 129 can be located external to the plant growth prediction system 120.

Example Plant Health Determination Use Case

As described herein, the plant growth prediction system 120 may be configured to determine current and/or predict future plant health instead of or in addition to predicting future plant growth. For example, the aerial vehicle controller 121 may receive flight path parameters from the user device 102 via the network 110. Once the aerial vehicle controller 121 determines that the aerial vehicle 130 should conduct a flight at a current time, a project member may bring the aerial vehicle 130 to the site (e.g., based on a reminder provided by the plant growth prediction system 120). The aerial vehicle controller 121 can transmit the flight path parameters to the aerial vehicle 130 over the network 110 and instruct the aerial vehicle 130 (e.g., the flight path controller 138) to begin the flight. The camera(s) 132 and/or a network interface (not shown) of the aerial vehicle 130 may transmit captured images to the image processor 122 in real-time (e.g., as the images are captured) and/or after the flight is complete.

The image processor 122 may implement a process to convert the captured images into plant health images. For example, the image processor 122 can process a captured image pixel by pixel. Each pixel may have an RGB color represented by a red value, a green value, and a blue value. For each pixel, the image processor 122 can identify the green value of the RGB color. The green value of the RGB color may indicate a relative health of a plant and/or whether the pixel depicts a portion of a plant or another object. Based on the magnitude of the green value, the image processor 122 can assign another RGB color to the pixel and convert the pixel from the original RGB color to the newly assigned RGB color. In an embodiment, the assigned RGB color may be a color within a color spectrum between red (e.g., RGB hexadecimal color #FF0000) and green (e.g., RGB hexadecimal color #00FF00), where orange (e.g., RGB hexadecimal color #FFA500) represents a middle color between red and green in the color spectrum. The higher the original green value of the pixel, the closer the newly assigned RGB color will be to green (e.g., RGB hexadecimal color #00FF00) and the farther the newly assigned RGB color will be from red (e.g., RGB hexadecimal color #FF0000). As an illustrative embodiment, if the original RGB color of the pixel is RGB hexadecimal color #340067, then the newly assigned RGB color may be RGB hexadecimal color #FF0000. If the original RGB color of the pixel is RGB hexadecimal color #1EFFB0, then the newly assigned RGB color may be RGB hexadecimal color #00FF00. The image processor 122 can use other similar techniques, such as visible atmospherically resistant index (VARI) or normalized difference vegetation index (NDVI), to convert the pixels of the captured images. Thus, the image processor 122 may normalize the RGB color of each pixel of a captured image to an RGB color within the color spectrum described above. By normalizing the RGB color of each pixel of a captured image, the image processor 122 may produce a converted image that indicates plant health and/or a chemical composition of various plants (e.g., chlorophyll levels of a plant, nitrogen levels of a plant, etc.).

Alternatively, the image processor 122 can transmit the captured images to an external system (not shown) and the external system can process the captured images to convert the pixels using the same or similar process. The external system can then transmit the converted images to the image processor 122.

Figure 6A:
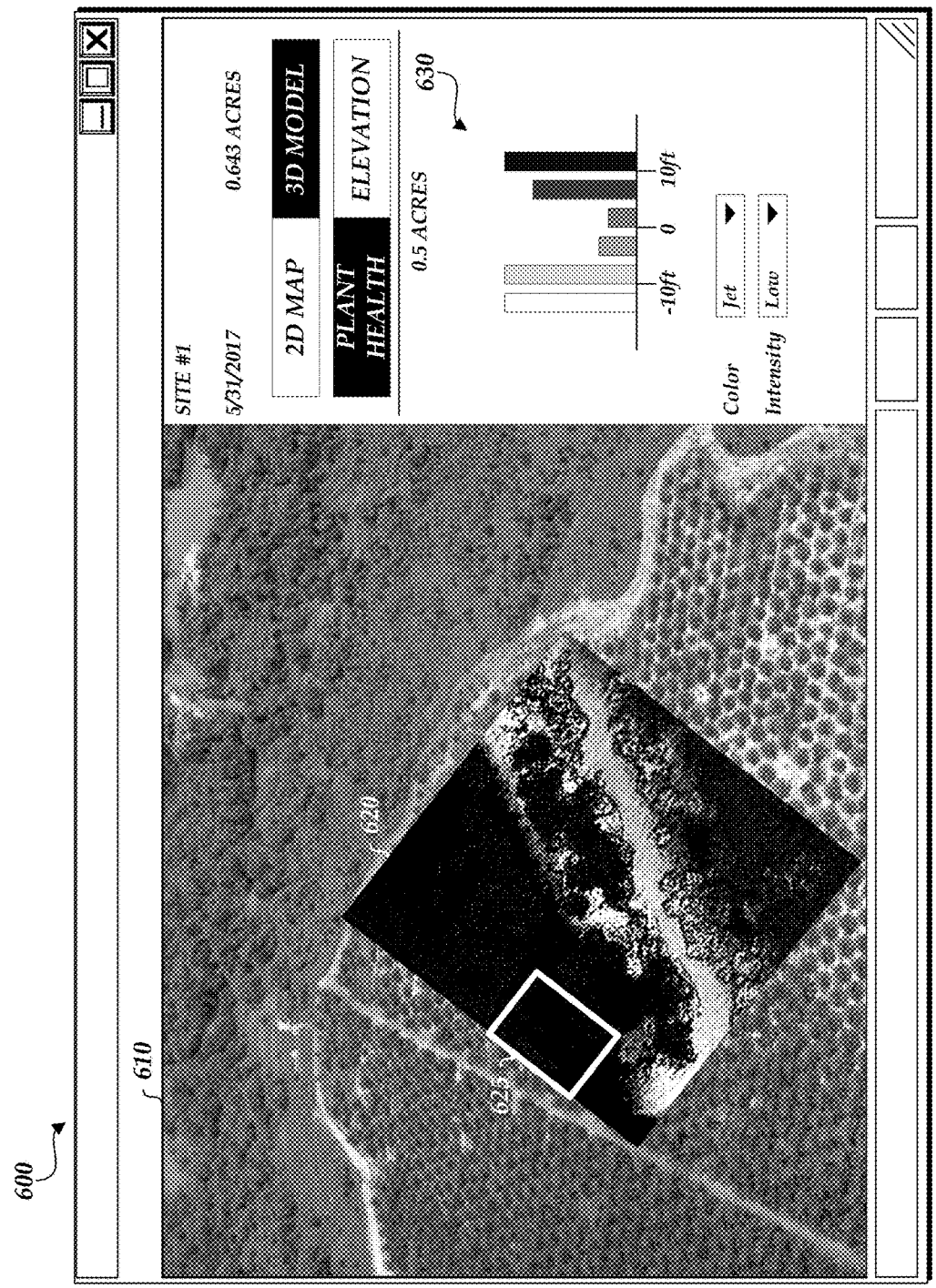
FIG. 6A illustrates a user interface displaying plant health of a site overlaid over a high-resolution image of the site depicted in a window.

The captured images that have pixels converted by the image processor 122 and/or external system may be referred to herein as plant health images. FIG. 6A depicts an example of a plant health image (shown as plant health data 620). The image processor 122 may further process the plant health images. For example, the image processor 122 can identify geographic coordinates corresponding to portions of the plant health image in which it appears that plants are unhealthy. An unhealthy plant may be any plant corresponding to one or more pixels that have a value less than a threshold value (e.g., less than RGB hexadecimal color #ADFF2F, less than RGB hexadecimal color #FFA500, etc.) within the above-described color spectrum. In some embodiments, sprinkler heads 156 of the irrigation system 150 or the irrigation system 150 itself may be located at specific geographic coordinates. Thus, the image processor 122 can transmit a message to a controller 152 of the irrigation system 150 (or an external network-based system, not shown, that manages the irrigation system 150) via the network 110 indicating the geographic coordinates corresponding to unhealthy plants. The controller 152 may manage the activation and deactivation of valves 154 controlling the flow of water to the sprinkler heads 156 and/or may control the activation of the sprinkler heads 156 themselves using a watering schedule. Thus, receipt of the message (either from the image processor 122 or the external network-based system) may cause the controller 152 of the irrigation system 150 to adjust its watering schedule such that the sprinkler heads 156 corresponding to the received geographic coordinates and/or the valves 154 controlling the flow of water to the sprinkler heads 156 corresponding to the received geographic coordinates are activated more frequently, may cause the controller 152 of the irrigation system 150 to automatically activate at least the sprinkler heads 156 corresponding to the received geographic coordinates and/or the valves 154 controlling the flow of water to the sprinkler heads 156 corresponding to the received geographic coordinates such that the sprinkler heads 156 spray water, and/or the like. Accordingly, the processing of the plant health images performed by the image processor 122 may result in an irrigation system 150 watering unhealthy plants more often.

Alternatively or in addition, the image processor 122 may process the plant health images to identify the height, width, volume, area, and/or canopy percentages of plants. For example, the image processor 122 can use object recognition techniques to identify individual plants (e.g., the image processor 122 can identify individual plants by identifying pixels that have a similar color, such as colors that are within a threshold value of each other). Once a plant is identified, the image processor 122 determines a width, volume, and/or area of the plant (e.g., based on the scale of the plant health image). For example, the image processor 122 can identify a boundary of the plant based on the pixel colors (e.g., a difference in pixel colors above a threshold value indicates a boundary of the plant) to determine the width, volume, and/or area of the plant. The image processor 122 can further determine a canopy percentage of the plant by measuring the area of the plant as a percentage of the total area of the site.

In addition, as the aerial vehicle 130 captures images, the aerial vehicle 130 may track an altitude of the aerial vehicle 130 (e.g., relative to the ground) and use a RADAR detector or other similar device to identify a distance between the aerial vehicle 130 and an object (e.g., a plant, the ground, water, etc.) below the aerial vehicle 130. At each location, the aerial vehicle 130 can subtract the identified distance from the tracked altitude to identify a height of an object below the aerial vehicle 130. Alternatively, the aerial vehicle 130 can transmit the tracked altitude and the identified distance to the image processor 122 and the image processor 122 can subtract the identified distance from the tracked altitude to identify a height of an object below the aerial vehicle 130 at various locations. In this way, the aerial vehicle 130 and/or image processor 122 can determine a height or heights (e.g., branches and leaves may be at different heights) of plants.

The image processor 122 can compare the determined height, width, volume, area, and/or canopy percentage of a plant or a group of plants within a geographic area to threshold heights, widths, volumes, areas, and/or canopy percentages to adjust lighting and/or lighting schedules, to adjust watering and/or watering schedules, and/or to identify when plants need to be pruned. For example, the image processor 122 can compare the height, width, volume, area, and/or canopy percentage of one plant (or one group of plants) against a threshold height, width, volume, area, and/or canopy percentage. If one or more of the height, width, volume, area, and/or canopy percentage values is greater than one or more of the threshold height, width, volume, area, and/or canopy percentage values by a threshold value or percentage, then this may indicate that the area beneath this plant (or group of plants) is generally dark. Thus, the image processor 122 can transmit a message to a lighting system (or an external network-based system, not shown, that manages the lighting system) via the network 110 indicating the geographic coordinates of this plant (or group of plants). Receipt of the message (either from the image processor 122 or the external network-based system) may cause the lighting system to adjust its schedule such that lights corresponding to the received geographic coordinates are activated earlier in the day and/or for a longer period of time, may cause the lighting system to automatically activate at least the lights corresponding to the received geographic coordinates, and/or the like. The image processor 122 may also generate a notification for transmission to a user device 102 via the network 110 (e.g., a push notification) indicating that the plant (or group of plants) need to be pruned.

Conversely, if one or more of the height, width, volume, area, and/or canopy percentage values is less than one or more of the threshold height, width, volume, area, and/or canopy percentage values by a threshold value or percentage, then this may indicate that the area beneath this plant (or group of plants) is generally light and the image processor 122 can transmit no message or a message to the lighting system (or the external network-based system) to perform the opposite operation (e.g., turn on the lights later and/or for a shorter period of time, automatically turn off the lights, etc.). Thus, the processing performed by the image processor 122 can be used to conserve energy via the efficient use of lighting. The image processor 122 may also generate a notification for transmission to a user device 102 via the network 110 (e.g., a push notification) indicating that the plant (or group of plants) do not need to be pruned, the plant (or group of plants) should be pruned later than scheduled, and/or additional plants should be planted in the corresponding geographic area. In addition, as described above, the image processor 122 can generate and transmit a message to cause the irrigation system 150 to water the plant (or group of plants) automatically and/or more frequently.

Figure 8A:
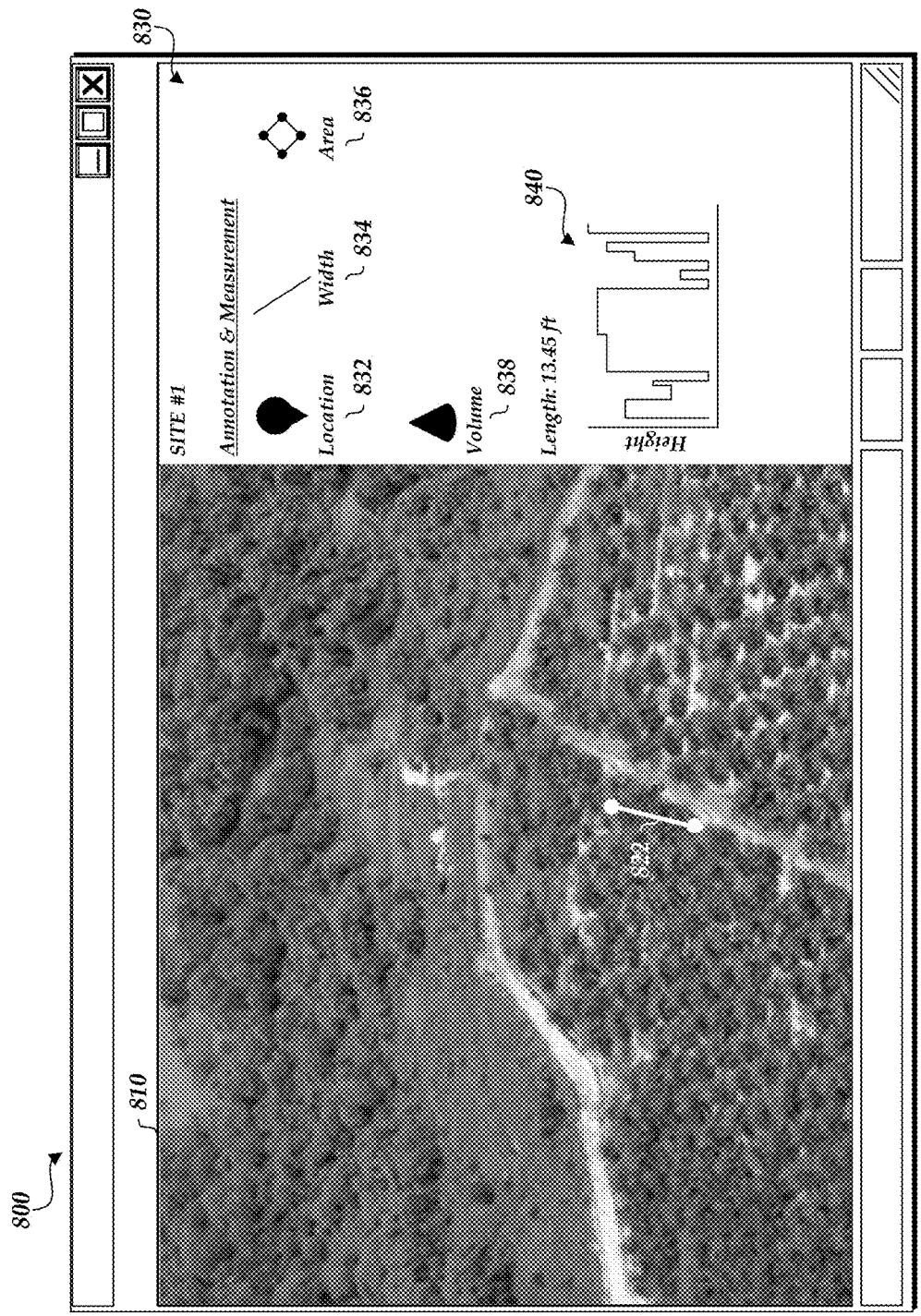
FIGS. 8A-8B illustrate a user interface 800 displaying tools for analyzing plants at a site depicted in a window 810.
Figure 8B:
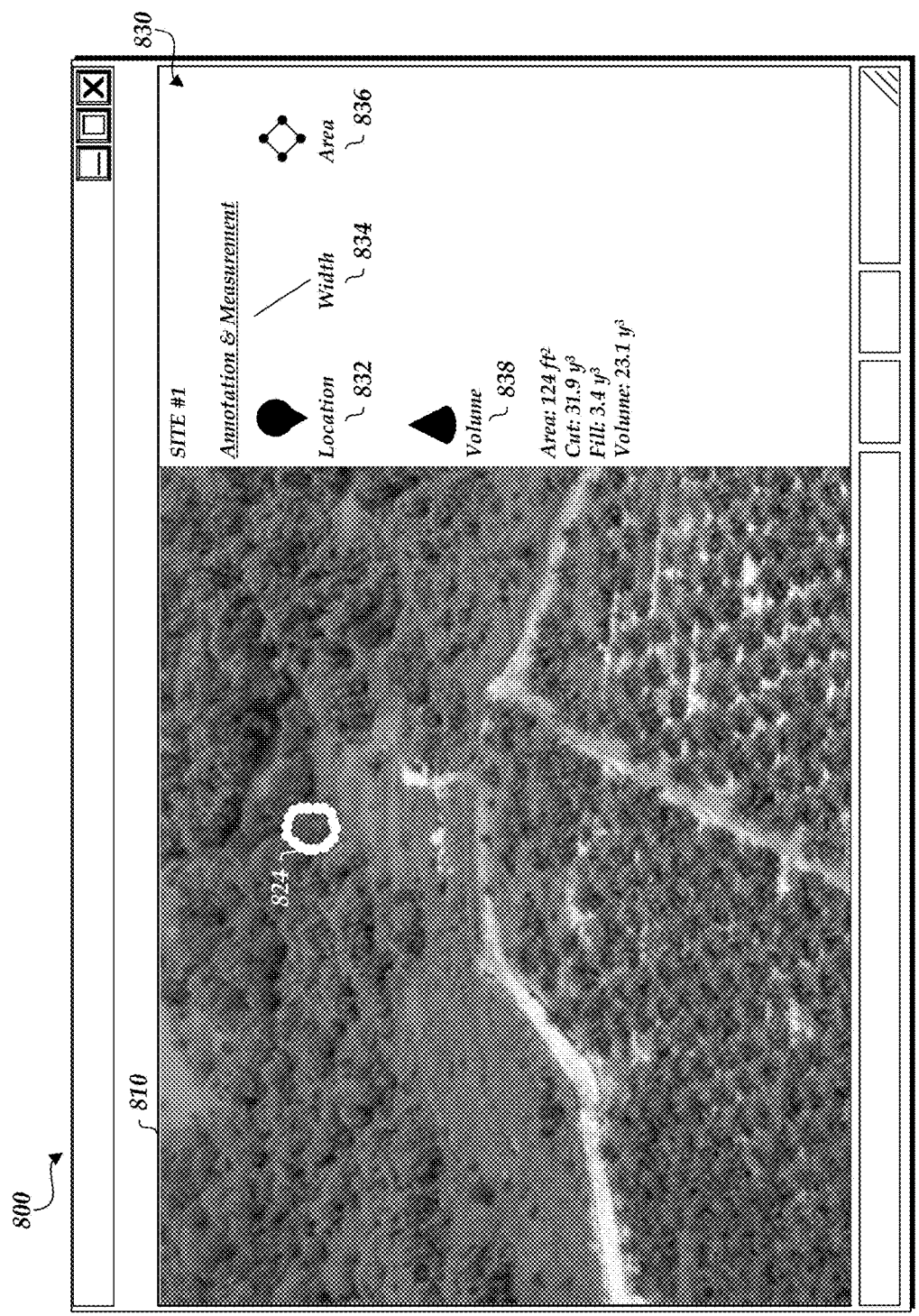

In some cases, the user interface generator 131 can generate user interface data that, when rendered by the user device 102, causes the user device 102 to display a user interface providing information on plant height, width, volume, area, and/or canopy percentage and/or tools for allowing a user to manually measure such information. For example, the user interface generator 131 may receive the captured images and/or the plant health images from the image processor 122 for display. Example user interfaces are depicted in FIGS. 8A-8B and are described in greater detail below.

Furthermore, the plant growth prediction system 120 can use similar techniques as described above with respect to predicting plant growth to predict plant health. For example, the diagnostic model generator 123 may receive, for a specific plant, the health of the plant (e.g., as represented by RGB hexadecimal colors) determined over a period of time via various images captured over a period of time. Using the plant health information, the diagnostic model generator 123 can generate a diagnostic model. The diagnostic model can be used to predict future plant health for that plant (e.g., represented by an RGB hexadecimal color). For example, the diagnostic model generator 123 can perform a linear regression analysis of the plant health, a cubic polynomial regression analysis of the plant health, and/or the like to generate the diagnostic model. The diagnostic model generator 123 may generate a different diagnostic model for each plant or for different sets of plants (e.g., plants that are within proximity of each other). The diagnostic model generator 123 can store the diagnostic models in the model data store 128.

The diagnostic models may output a plant health value as a function of time. Thus, the plant growth predictor 124 may then retrieve a diagnostic model for each plant at a site from the model data store 128 and use the diagnostic models to predict future plant health for one or more plants at various times in the future. The plant growth predictor 124 can package the predicted future plant health values into a report and/or provide the predicted future plant health values to the user interface generator 131 such that the user interface generator 131 can generate user interface data that, when rendered by the user device 102, causes the user device 102 to display the predicted future plant health values. As described above, the plant growth predictor 124 can also modify one or more captured images to indicate the predicted future plant health values. The plant growth indicator 124 can transmit the modified captured image(s) to the user device 102.

As described above, the image processor 122 can stitch the images received from the aerial vehicle 130 together to form a single stitched image. The image processor 122 can stitch the images before or after the images are converted into plant health images.

Example Block Diagrams for Determining and Predicting Plant Growth

Figure 2:
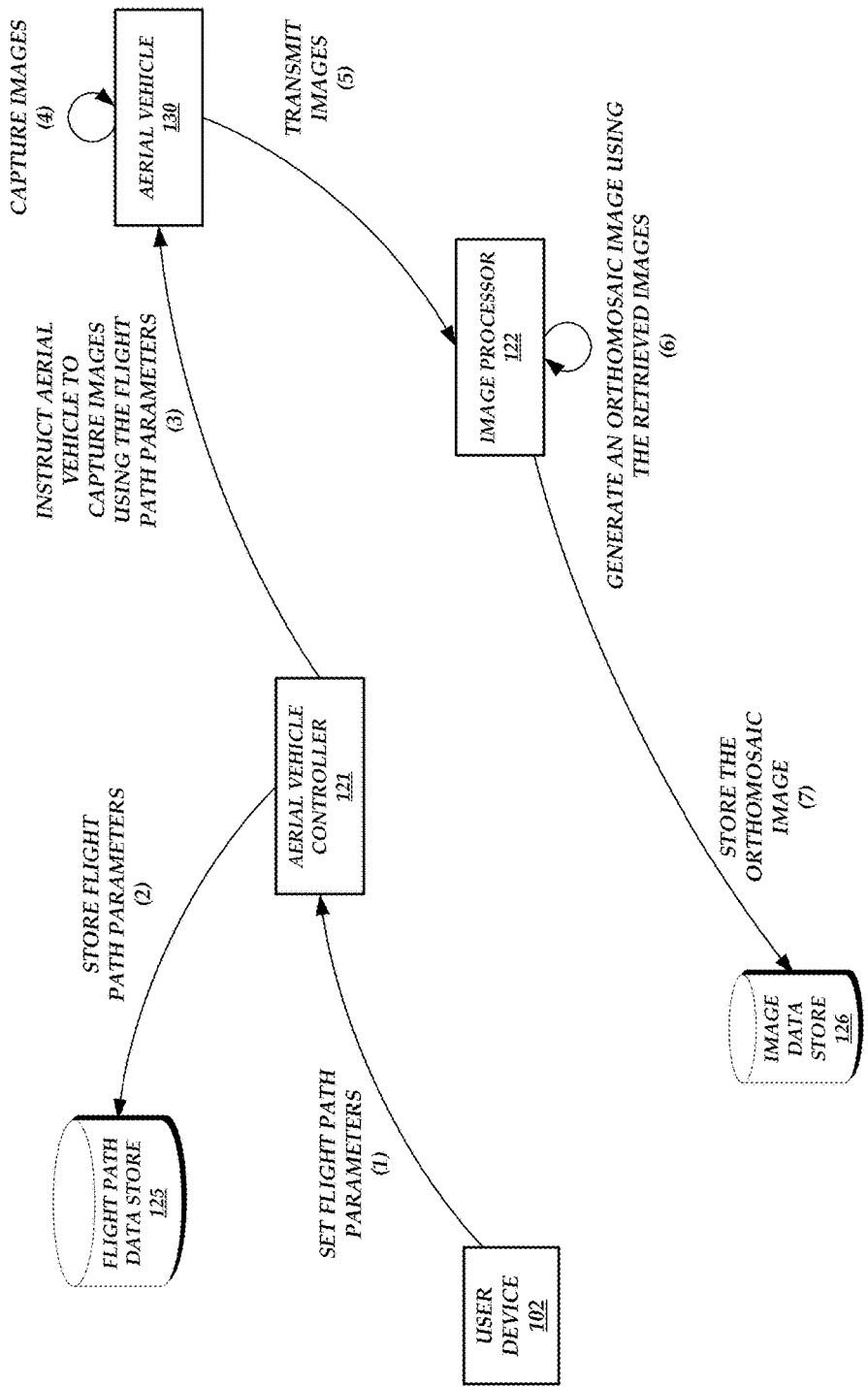
FIG. 2 is a flow diagram illustrating the operations performed by the components of the operating environment of FIG. 1 to generate an orthomosaic image for an initial flight, according to one embodiment.

FIG. 2 is a flow diagram illustrating the operations performed by the components of the operating environment 100 of FIG. 1 to generate an orthomosaic image for an initial flight, according to one embodiment. As illustrated in FIG. 2, the user device 102, based on input from a user, sets flight path parameters and transmits the flight path parameters to the aerial vehicle controller 121 at (1). The aerial vehicle controller 121 may then store the flight path parameters in the flight path data store 125 at (2). Before, during, or after storing the flight path parameters, the aerial vehicle controller 121 can instruct the aerial vehicle 130 at (3) to capture images using the flight path parameters.

In response to receiving the instruction to capture images, the aerial vehicle 130 can begin a flight and capture images at (4). As images are captured and/or after the flight is complete, the aerial vehicle 130 can transmit the captured images to the image processor 122 at (5).

The image processor 122 can generate an orthomosaic image using the retrieved images at (6). For example, the retrieved images may be both thermographic images and high-resolution images. The image processor 122 can stitch the thermographic images together and can stitch the high-resolution images together. The image processor 122 can then combine the stitched images to form an orthomosaic image in which the image is geometrically corrected with a uniform scale. The image processor 122 can then store the orthomosaic image in the image data store 126 at (7).

Figure 3A:
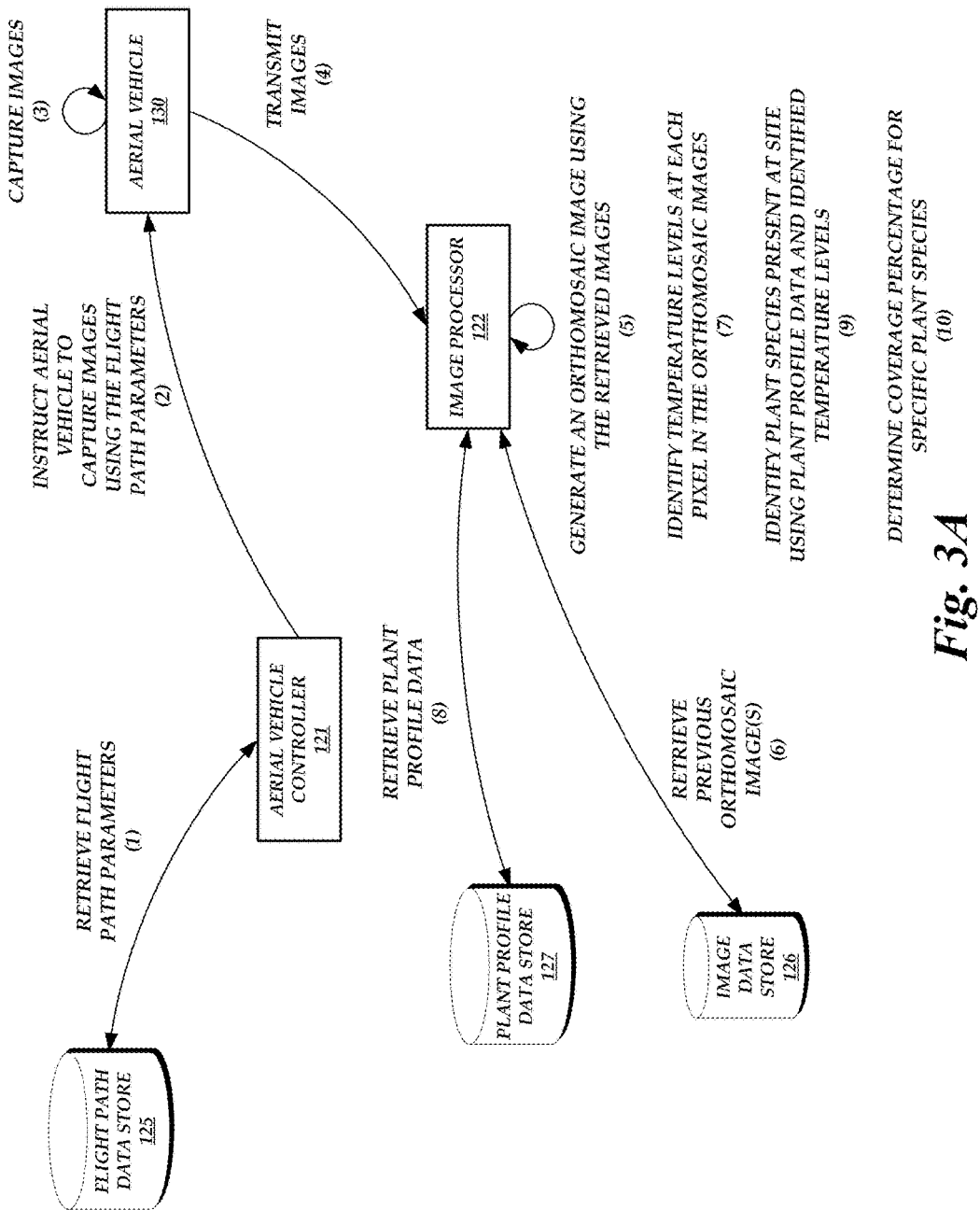
FIGS. 3A-3B are flow diagrams illustrating the operations performed by the components of the operating environment of FIG. 1 to predict plant growth after a flight that follows the initial flight, according to one embodiment.
Figure 3B:
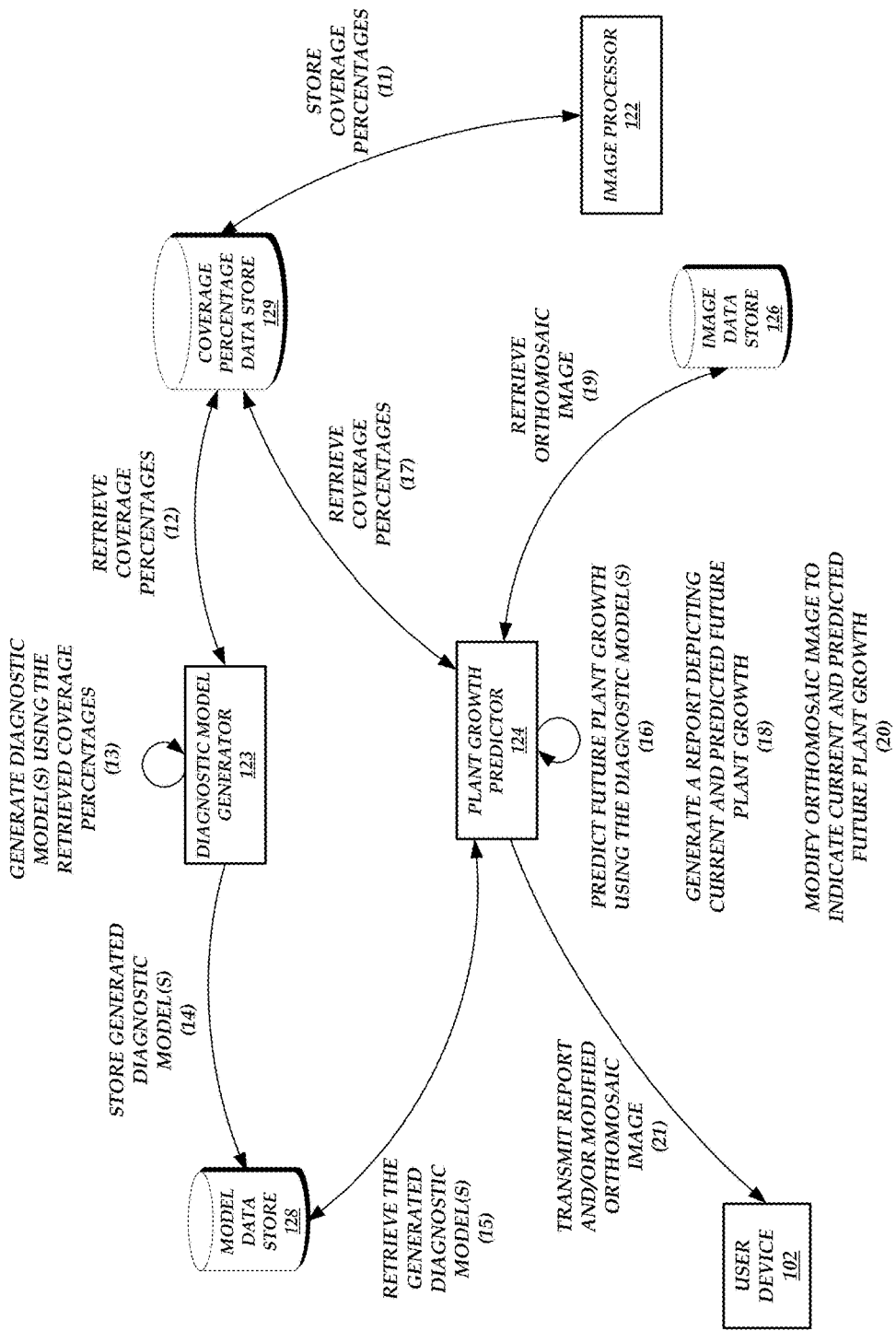

FIGS. 3A-3B are flow diagrams illustrating the operations performed by the components of the operating environment 100 of FIG. 1 to predict plant growth after a flight that follows the initial flight, according to one embodiment. As illustrated in FIG. 3A, the aerial vehicle controller 121 can retrieve flight path parameters from the flight path data store 125 at (1). For example, because this is a flight after the initial flight, the user device 102 may have already provided flight set parameters. The aerial vehicle controller 121 can then query the flight path data store 125 using an identification of the site to retrieve the appropriate flight path parameters. The aerial vehicle controller 121 may retrieve the flight path parameters at a time previously indicated by the user device 102 (e.g., the user device 102 may provide a set of times for using the aerial vehicle 130 to capture images and/or an indication when an event corresponding to a flight has commenced, such as when a site has been impacted). The aerial vehicle controller 121 may then instruct the aerial vehicle 130 at (2) to capture images using the flight path parameters.

In response to receiving the instruction to capture images, the aerial vehicle 130 can begin a flight and capture images at (3). As images are captured and/or after the flight is complete, the aerial vehicle 130 can transmit the captured images to the image processor 122 at (4).

The image processor 122 can generate an orthomosaic image using the retrieved images at (5). For example, the retrieved images may be both thermographic images and high-resolution images. The image processor 122 can stitch the thermographic images together and can stitch the high-resolution images together. The image processor 122 can then combine the stitched images to form an orthomosaic image in which the image is geometrically corrected with a uniform scale.

The image processor 122 can then retrieve previous orthomosaic images from the image data store 126 at (6). In each orthomosaic image, the image processor 122 can identify at (7) the brightness temperature levels of each pixel.

Before, during, or after identifying the brightness temperature levels, the image processor 122 can retrieve plant profile data from the plant profile data store 127 at (8). For example, the plant profile data may include mappings of plant species to brightness temperatures. Using the plant profile data, the image processor 122 can identify plant species corresponding to each pixel in each orthomosaic image and, therefore, the plant species that are present at the site at (9).

At a previous time, the user device 102 may provide the image processor 122 with a list of specific plant species to examine, such as an identification of native species, fill, and/or invasive species. The image processor 122 can use this information along with the identified plant species to determine at (10), in each orthomosaic image, a native species coverage percentage, a fill coverage percentage, and/or an invasive species coverage percentage. In addition, the image processor 122 can use the identified plant species information to determine, in each orthomosaic image, plant diversity at the site.

As illustrated in FIG. 3B, the image processor 122 stores the coverage percentages in the coverage percentage data store 129 at (11). At a later time, such as when the user device 102 requests a report, the diagnostic model generator 123 can retrieve the coverage percentages at (12). The diagnostic model generator 123 can use the coverage percentages to generate one or more diagnostic models at (13). For example, the diagnostic model generator 123 may generate a native species diagnostic model, a fill diagnostic model, an invasive species diagnostic model, and/or a plant diversity diagnostic model. The diagnostic model generator 123 can store the generated diagnostic model(s) in the model data store 128 at (14).

The plant growth predictor 124 can retrieve the generated diagnostic model(s) at (15) and use the diagnostic model(s) to predict future plant growth at the site at (16). For example, the plant growth predictor 124 can predict a time when a desired native species coverage percentage will be achieved. The plant growth predictor 124 can retrieve coverage percentages from the coverage percentage data store 129 at (17) and generate a report depicting the current and predicted future plant growth at (18) (e.g., where the current and predicted future plant growth is represented as a coverage percentage).

In further embodiments, the plant growth prediction system 120 can instruct other devices to perform actions in response to the results of the report. As an illustrative example, if the report generated for a current time period indicates that the current plant growth is 0%, whereas a previously generated report predicted that the plant growth during the current time period would be 10%, then the plant growth prediction system 120 can instruct a sprinkler system (e.g., the irrigation system 150) to modify a watering schedule such that the sprinklers (e.g., the sprinkler heads 156) in the sprinkler system water the site more often, instruct a vehicle or other like apparatus to release additional fertilizer in the site, transmit a notification to another device (e.g., the user device 102) instructing a user to add more water and/or fertilizer to the site or to otherwise adjust a plant growth plan, and/or the like.

In addition, the plant growth predictor 124 can retrieve an orthomosaic image from the image data store 126 at (19). For example, the plant growth predictor 124 may retrieve the latest orthomosaic image. The plant growth predictor 124 can then modify the orthomosaic image at (20) to indicate current and predicted future plant growth. For example, the orthomosaic image can be shaded with colors to differentiate between current and predicted future plant growth. The plant growth predictor 124 may then transmit the report and/or modified orthomosaic image to the user device 102 at (21).

Example Plant Growth Prediction Routine

Figure 4:
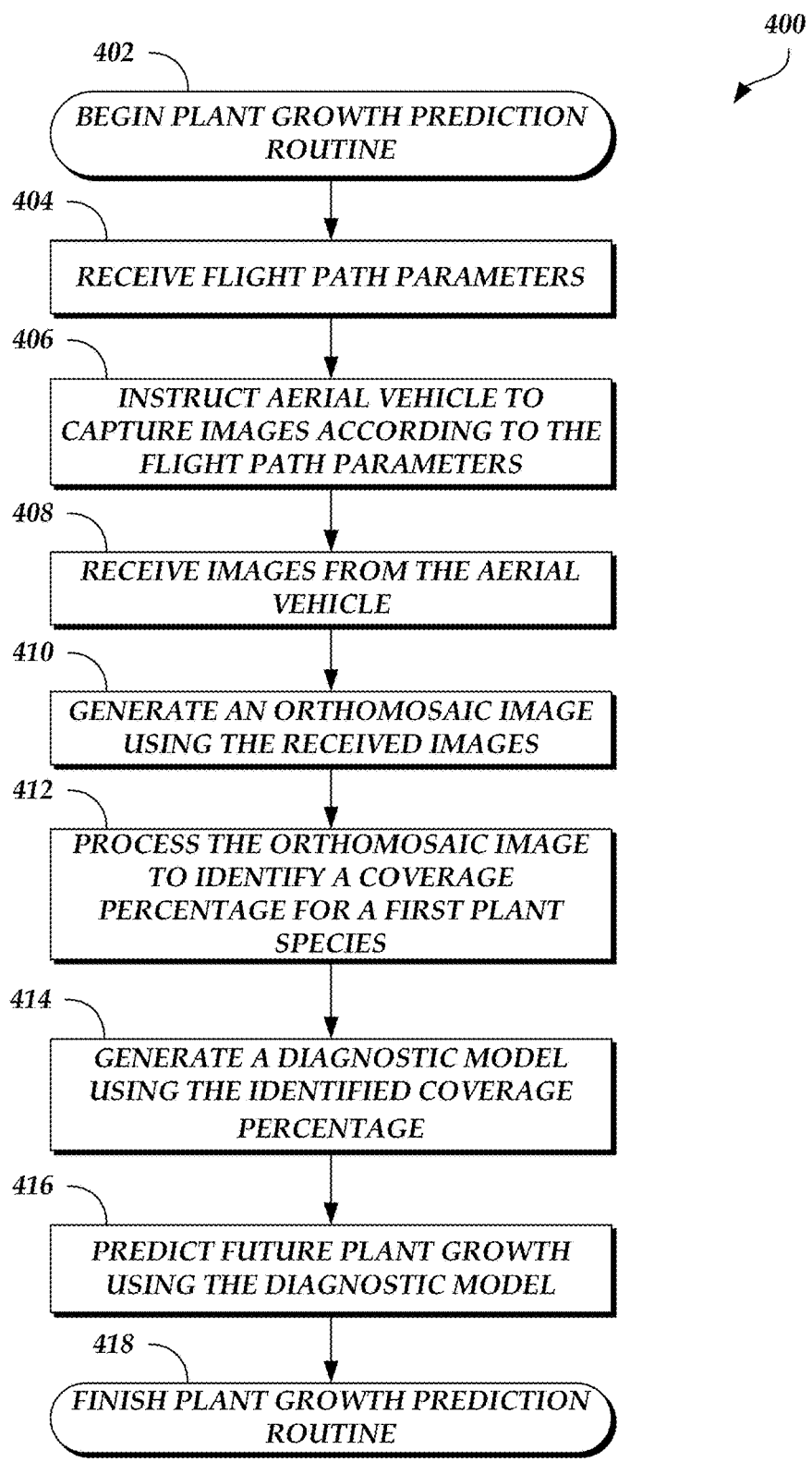
FIG. 4 is a flow diagram depicting a plant growth prediction routine illustratively implemented by a plant growth prediction system, according to one embodiment.

FIG. 4 is a flow diagram depicting a plant growth prediction routine 400 illustratively implemented by a plant growth prediction system, according to one embodiment. As an example, the plant growth prediction system 120 of FIG. 1 can be configured to execute the plant growth prediction routine 400. The plant growth prediction routine 400 begins at block 402.

At block 404, flight path parameters are received. For example, the flight path parameters can include a flight path, a shooting angle, a capture mode, a gimbal pitch angle, an end-mission action, and/or the like. The flight path parameters can be received from a user device 102 or the flight path data store 125.

At block 406, an aerial vehicle is instructed to captures images according to the flight path parameters. For example, the aerial vehicle may capture images using a thermal camera and a high-resolution camera.

At block 408, images are received from the aerial vehicle. For example, the images may be received in real-time and/or after the flight is complete.

At block 410, an orthomosaic image is generated using the received images. For example, the images captured by the thermal camera may be combined and the images captured by the high-resolution camera may be combined. The combined images may then be merged to form the orthomosaic image.

At block 412, the orthomosaic image is processed to identify a coverage percentage for a first plant species. For example the first plant species may be a native species of the site.

At block 414, a diagnostic model is generated using the identified coverage percentage. For example, the identified coverage percentage and one or more historical coverage percentages may be used to generate the diagnostic model.

At block 416, future plant growth is predicted using the diagnostic model. For example, a time when the plant growth reaches a desired coverage percentage may be predicted. After the future plant growth is predicted, the plant growth prediction routine 400 is complete, as shown at block 418.

Example User Interfaces

FIG. 5A illustrates a user interface 500 displaying a site 520 and a list 550 of basic flight path parameters. The user interface 500 may be displayed by a user device 102 based on a rendering of user interface data generated and provided by the plant growth prediction system 120 (e.g., the user interface generator 131).

As illustrated in FIG. 5A, the user interface 500 displays a window 510 that includes an image depicting the site 520. The depiction of the site 520 is modified with a flight path 522 of the aerial vehicle 130 that overlays the image of the site 520. As described herein, a user can generate the flight path 522 by, for example, dragging a cursor or touch input across the user interface 500. Alternatively or in addition, the user can enter in the user interface 500 a set of geographic coordinates and an order in which the geographic coordinates are to be reached, thereby forming the flight path 522. Each time a direction of the flight path 522 changes, a waypoint (e.g., represented by white circles) may be depicted in the flight path 522 at the point of the direction change. In addition, a starting position 524 of the flight path 522 may be indicated in the window 510 as well as a current location 530 of the aerial vehicle 130 if the aerial vehicle 130 is already in flight.

The window 510 may further include a box 540 indicating current parameters of the aerial vehicle 130. For example, the box 540 may include the direction, speed, latitude, longitude, and/or altitude of the aerial vehicle 130.

The list 550 of basic flight path parameters may include a mission type (e.g., 3DMap, 2DMap, etc.), an estimated flight time, a flight length (e.g., a length of the flight path 522), a number of waypoints in the flight path 522, a camera model, a shooting angle, a capture mode, a flight course mode, a aerial vehicle 130 speed, an aerial vehicle 130 altitude, geographic coordinates of a starting point (e.g., latitude and longitude), and/or a resolution of the camera.

There may be several types of shooting angles. For example, the parallel to main path shooting angle may cause a camera 132 to be positioned such that a lens of the camera 132 faces directly down (e.g., 90 degrees straight down) and is parallel with the ground and the vertical to main path shooting angle may cause a camera 132 to be positioned such that a lens of the camera 132 faces directly ahead or to the side of the aerial vehicle 130 and is perpendicular with the ground. In addition, the shooting angle may be selected to be an angle between parallel to main path and vertical to main path.

There may also be several types of capture modes. For example, the hover and capture at point capture mode results in a camera 132 capturing an image at each waypoint, the capture at equal time intervals capture mode results in a camera 132 capturing an image in set time intervals, and the capture at equal distance intervals results in a camera 132 capturing an image every threshold distance.

FIG. 5B illustrates a user interface 560 displaying the site 520 and a list 570 of advanced flight path parameters. The user interface 560 may be displayed by a user device 102 based on a rendering of user interface data generated and provided by the plant growth prediction system 120 (e.g., the user interface generator 131).

As illustrated in FIG. 5B, the list 570 of advanced flight path parameters can include some basic flight parameters (e.g., mission type, an estimated flight time, a flight length, a number of waypoints in the flight path 522, and geographic coordinates of a starting point), front overlap ratio, side overlap ratio, course angle, margin, gimbal pitch angle, and end-mission action.

If the user updates any of the basic or advanced flight path parameters in the user interfaces 500 or 560, this may cause the user device 102 to notify the aerial flight controller 121 of the update. The aerial flight controller 121 may then transmit an instruction to the flight path controller 138 to update the flight path according to the updated flight path parameter(s). Thus, the user may be able to update the flight path of the aerial vehicle 130 in real-time as the aerial vehicle 130 is in flight.

In further embodiments, not shown, the user interfaces 500 and/or 560 can display images captured by the aerial vehicle 130 as those images are captured. The images may be received by the user device 102 from the image processor 122.

FIG. 6A illustrates a user interface 600 displaying plant health data 620 of a site overlaid over a high-resolution image of the site depicted in a window 610. Thus, the combined images depicted in the window 610 may be an orthomosaic image. The user interface 600 may be displayed by a user device 102 based on a rendering of user interface data generated and provided by the plant growth prediction system 120 (e.g., the plant growth predictor 124). As an example, the plant growth prediction system 120 may be configured to determine current and/or predict future plant health for the purposes of the embodiment disclosed in FIG. 6A. The plant growth prediction system 120 may be configured to determine current and/or predict future plant health instead of or in addition to predicting future plant growth. The depicted plant health data 620 may be current plant health determined by the plant growth prediction system 120 and/or future plant health predicted by the plant growth prediction system 120.

As described herein, the plant growth predictor 124 can transmit a report and/or a modified orthomosaic image to the user device 102 to show current levels and/or predicted future levels. In further embodiments, the modified orthomosaic image can be appended with additional information that can be displayed in a user interface, such as the user interface 600. For example, as illustrated in FIG. 6A, the modified orthomosaic image can be appended with information identifying a size of the site (e.g., 0.643 acres), a date, a histogram 630, and options to modify the format in which the modified orthomosaic image is displayed (e.g., color options can be changed to jet, black and white, grayscale, etc.; intensity options can be changed to low, medium, high, etc.). The histogram 630 may show a quantity or percentage of plants in the site that have a particular health. Each health level may correspond to a shaded color (e.g., an RGB value, a grayscale value, etc.). The health levels can be absolute values or normalized (e.g., on a scale from −1 to 1, where −1 is the unhealthiest level and 1 is the healthiest level).

The orthomosaic image may be modified with box 625. Box 625 may be added to the orthomosaic image by the plant growth predictor 124 to indicate that if the plants in the portion of the site within box 625 become healthier (e.g., to a certain plant health level), then the desired coverage percentage will be reached.

Figure 6B:
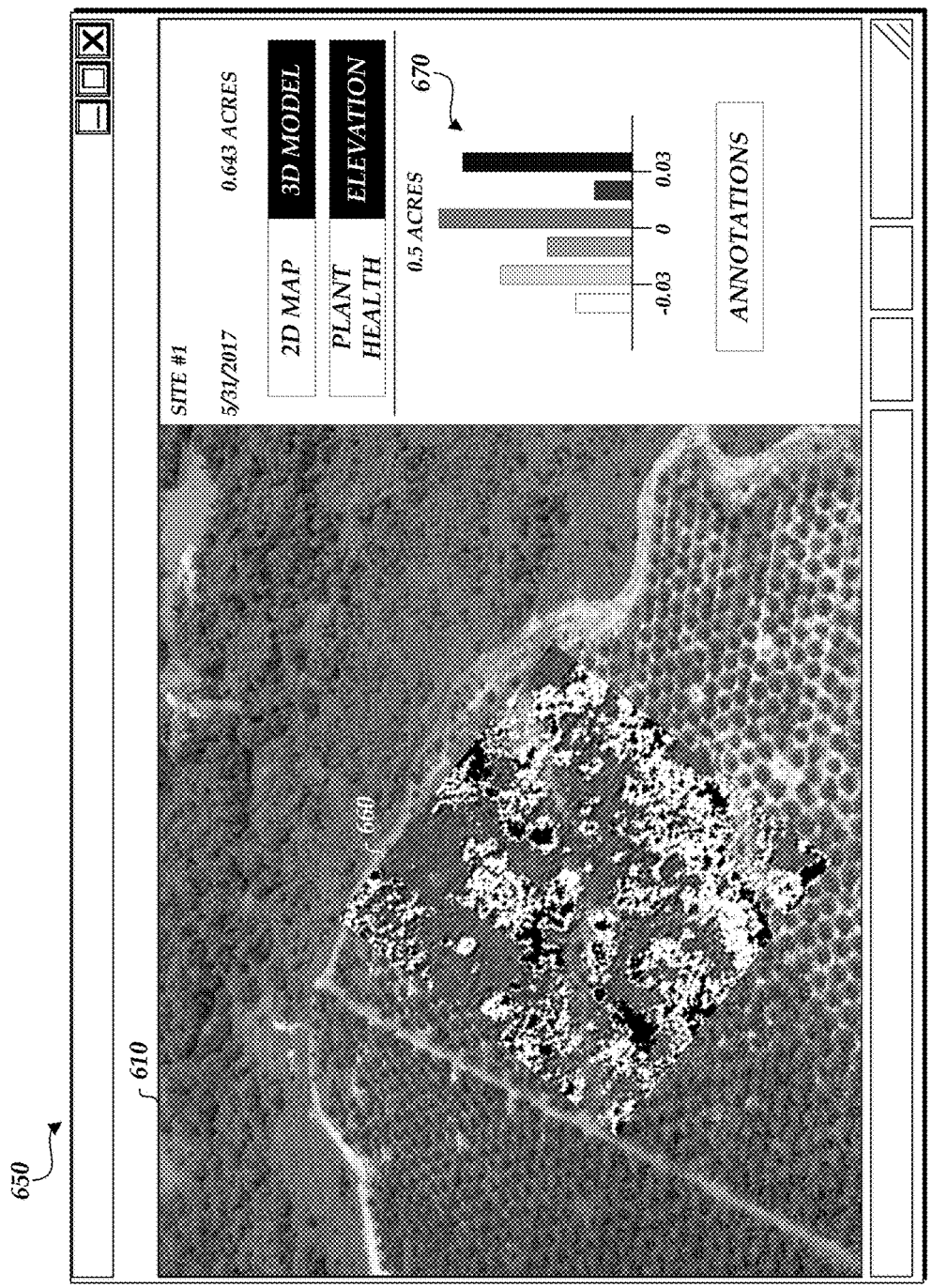
FIG. 6B illustrates a user interface displaying elevation of a site overlaid over a high-resolution image of the site depicted in the window.

FIG. 6B illustrates a user interface 650 displaying elevation 660 of a site overlaid over a high-resolution image of the site depicted in the window 610. Thus, the combined images depicted in the window 610 may also be an orthomosaic image. The user interface 650 may be displayed by a user device 102 based on a rendering of user interface data generated and provided by the plant growth prediction system 120 (e.g., the plant growth predictor 124). As an example, the plant growth prediction system 120 may be configured to determine current and/or predict future soil elevations (e.g., in light of possible erosion) for the purposes of the embodiment disclosed in FIG. 6B. The depicted elevation 620 may be current elevation determined by the plant growth prediction system 120 and/or future elevation predicted by the plant growth prediction system 120.

As illustrated in FIG. 6B, the orthomosaic image is appended with a size of the site (e.g., 0.643 acres), a date, a histogram 670, and options to annotate the orthomosaic image. The histogram 670 may show a quantity or percentage of terrain in the site that has a particular elevation. Each elevation level may correspond to a shaded color (e.g., an RGB value, a grayscale value, etc.).

Figure 7:
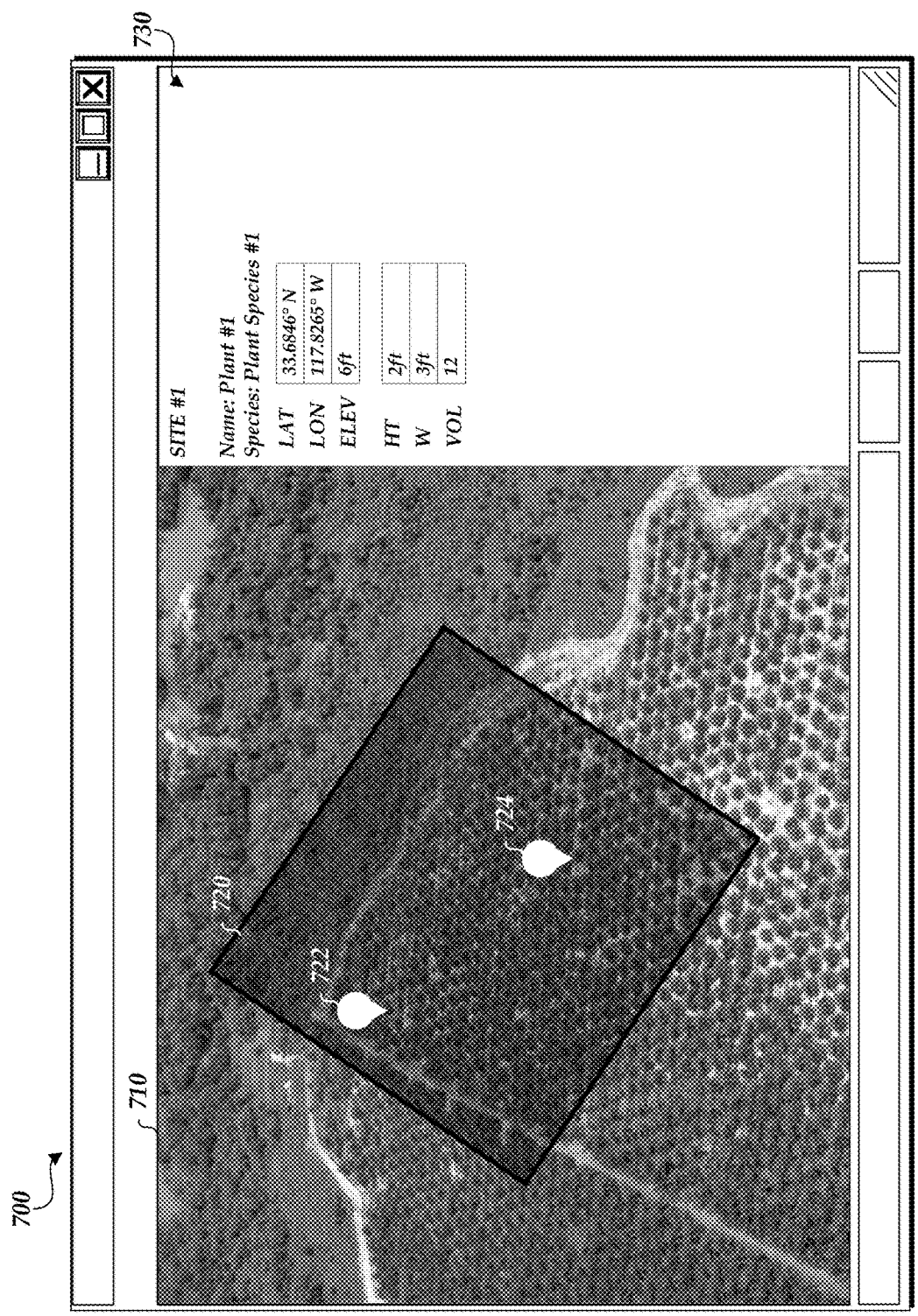
FIG. 7 illustrates a user interface 700 displaying individually identified plants in a site overlaid over a high-resolution image of the site depicted in a window.

FIG. 7 illustrates a user interface 700 displaying individually identified plants in a site overlaid over a high-resolution image of the site depicted in a window 710. The user interface 700 may be displayed by a user device 102 based on a rendering of user interface data generated and provided by the plant growth prediction system 120 (e.g., the user interface generator 131).

As illustrated in FIG. 7, the window 710 includes a transect 720 that may have been selected by a user. Within the transect 720, two individual plants are labeled: plant 722 and plant 724. The plants 722 and 724 may be labeled by the image processor 122 after the image processor 122 compares individual pixels of the high-resolution image to mappings between brightness temperature and plant species. The labeled plants 722 and 724 may be selectable.

In window 730, the user interface 700 may display information for a selected plant. For example, the window 730 may display a name of the selected plant, a species of the plant, geographic coordinates of the selected plant, an elevation at which the selected plant is situated, a height of the selected plant, a width of the selected plant, and/or a volume of the selected plant. The user may have the option, not shown, of viewing high-resolution images of the transect 720 taken at different times to view the change in plants 722 and/or 724 over time.

FIGS. 8A-8B illustrate a user interface 800 displaying tools for analyzing plants at a site depicted in a window 810. The user interface 800 may be displayed by a user device 102 based on a rendering of user interface data generated and provided by the plant growth prediction system 120 (e.g., the user interface generator 131).

As illustrated in FIG. 8A, the user interface 800 may include a window 830 that includes a location button 832, a width button 834, an area button 836, and a volume button 838. Selection of the location button 832 may allow a user to select a plant in the window 810. Selection of the width button 834 may allow a user to measure the width of a plant. For example, the user may be able to place a line 822 in the window 810. Creation of the line 822 causes the window 830 to indicate the length or distance covered by the line 822 (e.g., 13.45 ft). In addition, creation of the line 822 causes the window 830 to display a line graph 840 indicating a height of the plant or plants covered by the line 822. For example, plants may include branches, leaves, and/or the like location at various heights. The plants may also not completely cover a certain area (when looking at the plant from above) due to gaps between branches, leaves, and/or the like. Thus, the height of a plant may vary. The line graph 840 indicates, for each point along the line 822, the height of the plant or plants at the respective point along the line 822.

Selection of the area button 836 may allow a user to measure an area of a plant. For example, as illustrated in FIG. 8B, the user may be able to create a polygon 824 representing the outer boundaries of a plant. Creation of the polygon 824 causes the window 830 to indicate an area, cut, fill, and/or volume covered by the polygon 824 (e.g., 124 ft$^2$, 31.9 y$^3$, 3.4 y$^3$, and 23.1 y$^3$, respectively).

Example Plant Health Detection Routine

Figure 9:
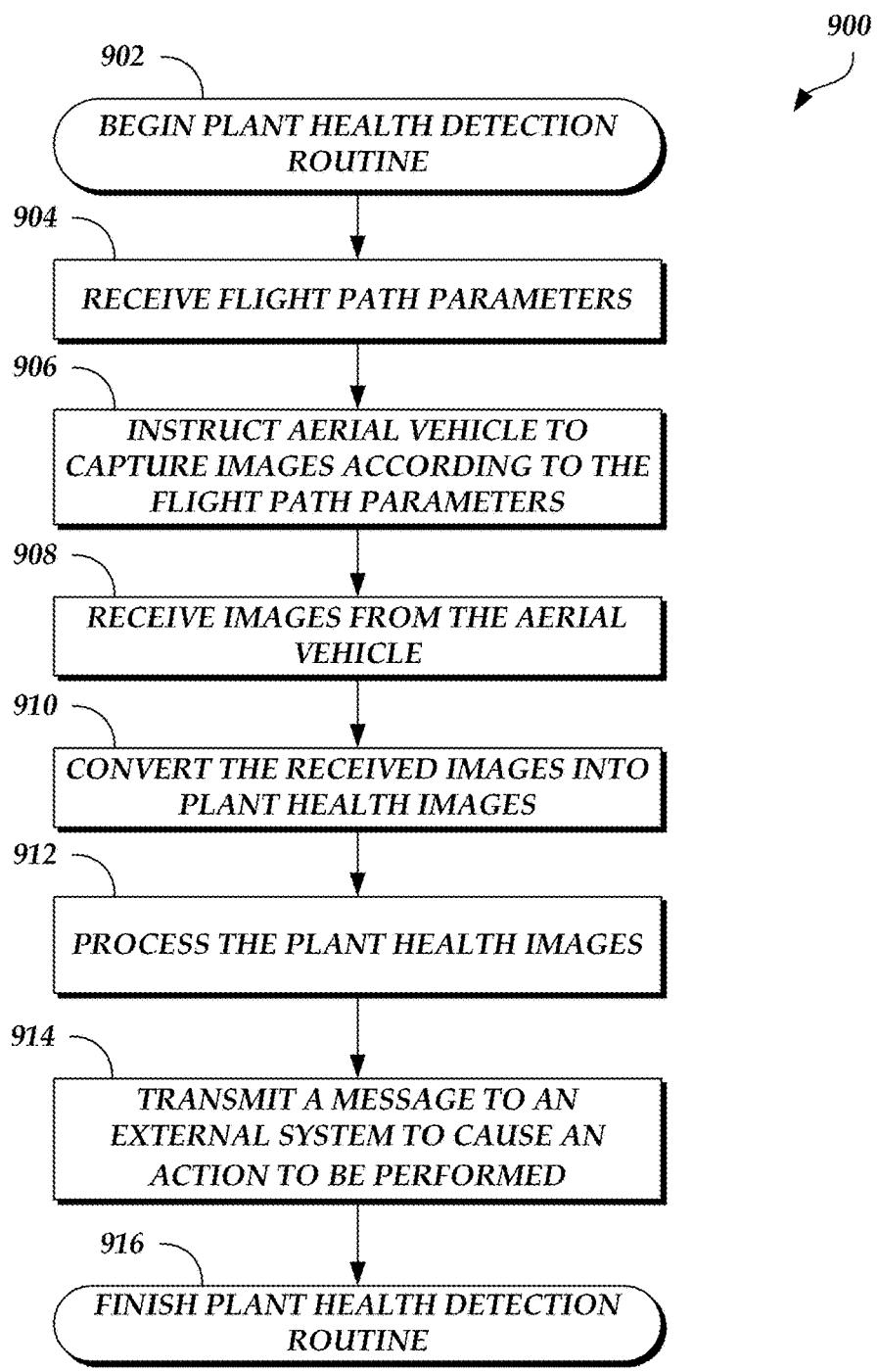
FIG. 9 is a flow diagram depicting a plant health prediction routine 900 illustratively implemented by a plant growth prediction system, according to one embodiment.

FIG. 9 is a flow diagram depicting a plant health prediction routine 900 illustratively implemented by a plant growth prediction system, according to one embodiment. As an example, the plant growth prediction system 120 of FIG. 1 can be configured to execute the plant health prediction routine 900. The plant health prediction routine 900 begins at block 902.

At block 904, flight path parameters are received. For example, the flight path parameters can include a flight path, a shooting angle, a capture mode, a gimbal pitch angle, an end-mission action, and/or the like. The flight path parameters can be received from a user device 102 or the flight path data store 125.

At block 906, an aerial vehicle is instructed to captures images according to the flight path parameters. For example, the aerial vehicle may capture images using a thermal camera and/or a high-resolution camera.

At block 908, images are received from the aerial vehicle. For example, the images may be received in real-time and/or after the flight is complete.

At block 910, the received images are converted into plant health images. For example, the image processor 122 can use the green value of the RGB color of a pixel to identify a new RGB color for the pixel and convert the pixel to the new RGB color.

At block 912, the plant health images are processed. For example, the image processor 122 can process the plant health images to identify the height, width, volume, area, and/or canopy percentages of plants. The image processor 122 can then compare the identified heights, widths, volumes, areas, and/or canopy percentages with threshold heights, widths, volumes, areas, and/or canopy percentages.

At block 914, a message is transmitted to an external system to cause an action to be performed. For example, based on the comparison performed by the image processor 122, the image processor 122 may prepare a message for transmission to an external system. The external system may be the irrigation system 150, a lighting system, and/or the like. Receipt of the message may cause the external system to perform an action, such as adjusting lighting and/or lighting schedules, adjusting watering and/or watering schedules, and/or notifying when plants need to be pruned. After the message is transmitted to the external system, the plant health detection routine 900 is complete, as shown at block 916.

Example Aerial Vehicle

Figure 10:
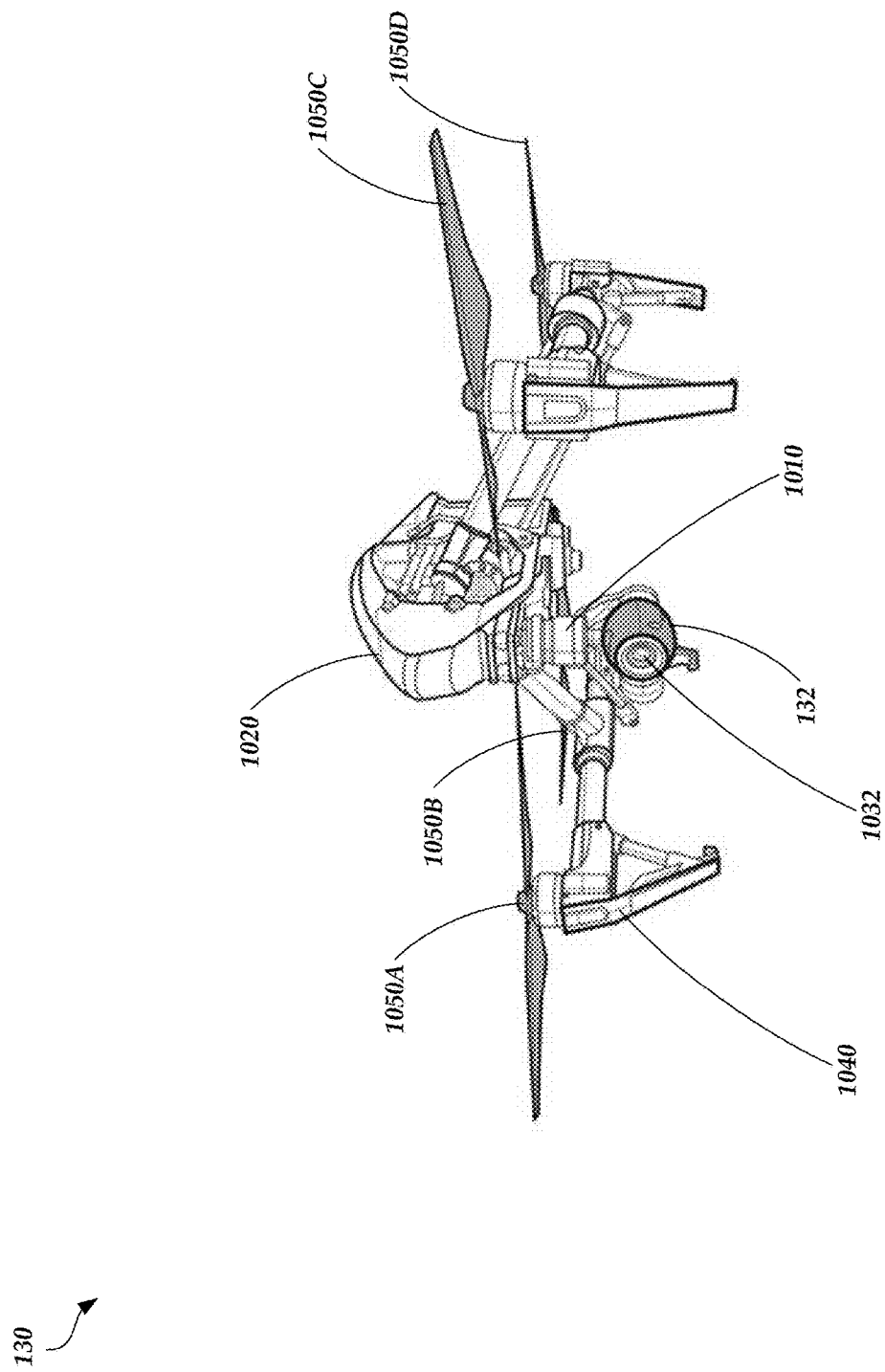
FIG. 10 illustrates an exemplary aerial vehicle, such as the aerial vehicle of FIG. 1.

FIG. 10 illustrates an exemplary aerial vehicle 130. As illustrated in FIG. 10, the aerial vehicle 130 is an unmanned aerial vehicle in which a camera 132 is coupled to a body 1020 of the aerial vehicle 130 via a gimbal 1010. The aerial vehicle 130 further includes four rotors 1050A-D. For example, the exemplary aerial vehicle 130 illustrated in FIG. 10 may be the INSPIRE 1 PRO drone. While the exemplary aerial vehicle 130 illustrated in FIG. 10 includes four rotors 1050A-D, this is not mean to be limiting. For example, the aerial vehicle 130 may include any number of rotors (e.g., six, eight, ten, twelve, etc.).

The gimbal 1010 may allow the camera 132 to rotate 360 degrees within a horizontal plane (e.g., a plane that extends from a left side of the aerial vehicle 130 to a right side of the aerial vehicle 130, a plane that extends from a back side of the aerial vehicle 130 to a front side of the aerial vehicle 130, etc.). As an illustrative example, the gimbal 1010 may allow the camera 132 to be positioned such that a lens 1032 of the camera 132 faces a right-front rotor apparatus 1040.

Similarly, the gimbal 1010 may allow the camera 132 to rotate at least 180 degrees within a vertical plane (e.g., a plane that extends from a top side of the aerial vehicle 130 to a bottom side of the aerial vehicle 130). As an illustrative example, the gimbal 1010 may allow the camera 132 to be positioned such that the lens 1032 faces a surface directly below the body 1020 of the aerial vehicle 130.

Additional Embodiments

Various example user devices 102 are shown in FIG. 1, including a desktop computer, laptop, and a mobile phone, each provided by way of illustration. In general, the user devices 102 can be any computing device such as a desktop, laptop or tablet computer, personal computer, wearable computer, server, personal digital assistant (PDA), hybrid PDA/mobile phone, mobile phone, electronic book reader, set-top box, voice command device, camera, digital media player, and the like. A user device 102 may execute an application (e.g., a browser, a stand-alone application, etc.) that allows a user to view captured images, set flight path parameters, modify a flight path during flight, and/or view predictions and associated annotated orthomosaic images.

The network 110 may include any wired network, wireless network, or combination thereof. For example, the network 110 may be a personal area network, local area network, wide area network, over-the-air broadcast network (e.g., for radio or television), cable network, satellite network, cellular telephone network, or combination thereof. As a further example, the network 110 may be a publicly accessible network of linked networks, possibly operated by various distinct parties, such as the Internet. In some embodiments, the network 110 may be a private or semi-private network, such as a corporate or university intranet. The network 110 may include one or more wireless networks, such as a Global System for Mobile Communications (GSM) network, a Code Division Multiple Access (CDMA) network, a Long Term Evolution (LTE) network, or any other type of wireless network. The network 110 can use protocols and components for communicating via the Internet or any of the other aforementioned types of networks. For example, the protocols used by the network 110 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or logic circuitry that implements a state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system for predicting plant growth, the system comprising:
an unmanned aerial vehicle, wherein the unmanned aerial vehicle comprises a first camera and a second camera; and
a computing system comprising one or more computing devices, wherein the computing system is configured to communicate with the unmanned aerial vehicle and configured with specific computer-executable instructions to:
instruct the unmanned aerial vehicle to capture a first set of images using the first camera and a second set of images using the second camera while flying along a flight path;

receive the first set of images and the second set of images from the unmanned aerial vehicle;
generate an orthomosaic image using the first set of images and the second set of images;
process the orthomosaic image to identify a percentage of a land parcel that is covered by a first plant species;
generate a diagnostic model using the identified percentage of the land parcel that is covered by the first plant species; and
predict future plant growth using the diagnostic model.

2. The system of claim 1, wherein the computing system is further configured with specific computer-executable instructions to:
combine the first set of images according to geographic coordinates associated with each image in the first set to form a combined first image;
combine the second set of images according to geographic coordinates associated with each image in the second set to form a combined second image; and
orthorectify the combined first image and the combined second image to generate the orthomosaic image.

3. The system of claim 1, wherein the first camera comprises a thermal imaging camera.

4. The system of claim 3, wherein each pixel in each image in the first set corresponds to a brightness temperature, and wherein each pixel in the orthomosaic image corresponds to a brightness temperature.

5. The system of claim 4, wherein the computing system is further configured with specific computer-executable instructions to:
retrieve data indicating that the first plant species is associated with a first brightness temperature;
process the orthomosaic image to identify that a first set of pixels of the orthomosaic image correspond to the first brightness temperature;
determine that the first set of pixels are a first percentage of a total number of pixels in the orthomosaic image; and
determine that the percentage of the land parcel that is covered by the first plant species equals the first percentage.

6. The system of claim 4, wherein the computing system is further configured with specific computer-executable instructions to:
retrieve data indicating that the first plant species is associated with a first brightness temperature;
process the orthomosaic image to identify that a first pixel of the orthomosaic image corresponds to the first brightness temperature; and
identify a first plant at the first pixel, wherein the first plant is an individual plant of the first plant species.

7. The system of claim 4, wherein the computing system is further configured with specific computer-executable instructions to identify a health of a plant at a first pixel of the orthomosaic image based on the brightness temperature of the first pixel.

8. The system of claim 1, wherein the identified percentage of the land parcel that is covered by the first plant species is the percentage of the land parcel that is covered by the first plant species at a first time, and wherein the computing system is further configured with specific computer-executable instructions to:
retrieve data indicating a second percentage of the land parcel that was covered by the first plant species at a second time before the first time; and
perform a linear regression analysis on at least one of the percentage, the second percentage, the first time, and the second time to generate the diagnostic model.

9. The system of claim 1, wherein the computing system is further configured with specific computer-executable instructions to identify a predicted time when a percentage of the land parcel that is covered by the first plant species equals a desired percentage.

10. The system of claim 1, wherein the computing system is further configured with specific computer-executable instructions to:
modify the orthomosaic image to indicate a portion of the land parcel at which the first plant species needs to grow such that a percentage of the land parcel that is covered by the first plant species equals a desired percentage; and
transmit the modified orthomosaic image to a user device.

11. The system of claim 1, wherein the computing system is further configured with specific computer-executable instructions to:
receive flight path parameters from a user device over a network; and
instruct the unmanned aerial vehicle to capture the first set of images using the first camera and the second set of images using the second camera while flying along a flight path in a manner defined by the flight path parameters.

12. The system of claim 11, wherein the flight path parameters comprise at least one of geographic coordinates, waypoints, flight length, flight time, speed, altitude, camera shooting angle, camera capture mode, or camera resolution.

13. A computer-implemented method of predicting plant growth, the method comprising:
as implemented by one or more computing devices configured with specific computer-executable instructions,
instructing an aerial vehicle to commence a flight along a flight path such that the aerial vehicle captures a first set of images using a first camera and captures a second set of images using a second camera;
receiving the first set of images and the second set of images from the aerial vehicle;
generating an orthomosaic image using the first set of images and the second set of images;
processing the orthomosaic image to identify a percentage of a land parcel that is covered by a first plant species;
generating a diagnostic model using the identified percentage of the land parcel that is covered by the first plant species; and
predicting future plant growth using the diagnostic model.

14. The computer-implemented method of claim 13, wherein generating an orthomosaic image using the first set of images and the second set of images further comprises:
combining the first set of images according to geographic coordinates associated with each image in the first set to form a combined first image;
combining the second set of images according to geographic coordinates associated with each image in the second set to form a combined second image; and
orthorectifying the combined first image and the combined second image to generate the orthomosaic image.

15. The computer-implemented method of claim 13, wherein the first camera comprises a thermal imaging camera.

16. The computer-implemented method of claim 15, wherein each pixel in each image in the first set corresponds to a brightness temperature, and wherein each pixel in the orthomosaic image corresponds to a brightness temperature.

17. The computer-implemented method of claim 16, wherein processing the orthomosaic image to identify a percentage of a land parcel that is covered by a first plant species further comprises:
retrieving data indicating that the first plant species is associated with a first brightness temperature;
processing the orthomosaic image to identify that a first set of pixels of the orthomosaic image correspond to the first brightness temperature;
determining that the first set of pixels are a first percentage of a total number of pixels in the orthomosaic image; and
determining that the percentage of the land parcel that is covered by the first plant species equals the first percentage.

18. The computer-implemented method of claim 16, further comprising:
retrieving data indicating that the first plant species is associated with a first brightness temperature;
processing the orthomosaic image to identify that a first pixel of the orthomosaic image corresponds to the first brightness temperature; and
identifying a first plant at the first pixel, wherein the first plant is an individual plant of the first plant species.

19. The computer-implemented method of claim 16, further comprising identifying a health of a plant at a first pixel of the orthomosaic image based on the brightness temperature of the first pixel.

20. The computer-implemented method of claim 13, wherein the identified percentage of the land parcel that is covered by the first plant species is the percentage of the land parcel that is covered by the first plant species at a first time, and wherein generating a diagnostic model using the identified percentage of the land parcel that is covered by the first plant species further comprises:
retrieving data indicating a second percentage of the land parcel that was covered by the first plant species at a second time before the first time; and
performing a linear regression analysis on at least one of the percentage, the second percentage, the first time, and the second time to generate the diagnostic model.

21. Non-transitory, computer-readable storage media comprising computer-executable instructions for predicting plant growth, wherein the computer-executable instructions, when executed by a computer system, cause the computer system to:
instruct an aerial vehicle to commence a flight along a flight path such that the aerial vehicle captures a first set of images using a first camera;
process the first set of images received from the aerial vehicle;
generate an orthomosaic image using the first set of images;
process the orthomosaic image to identify a percentage of a land parcel that is covered by a first plant species;
generate a diagnostic model using the identified percentage of the land parcel that is covered by the first plant species; and
predict future plant growth using the diagnostic model.

22. The non-transitory, computer-readable storage media of claim 21, wherein the first camera comprises a thermal imaging camera, wherein each pixel in each image in the first set corresponds to a brightness temperature, and wherein each pixel in the orthomosaic image corresponds to a brightness temperature.

23. The non-transitory, computer-readable storage media of claim 22, wherein the computer-executable instructions further cause the computer system to:
retrieve data indicating that the first plant species is associated with a first brightness temperature;
process the orthomosaic image to identify that a first set of pixels of the orthomosaic image correspond to the first brightness temperature;
determine that the first set of pixels are a first percentage of a total number of pixels in the orthomosaic image; and
determine that the percentage of the land parcel that is covered by the first plant species equals the first percentage.

24. The non-transitory, computer-readable storage media of claim 21, wherein the identified percentage of the land parcel that is covered by the first plant species is the percentage of the land parcel that is covered by the first plant species at a first time, and wherein the computer-executable instructions further cause the computer system to:
retrieve data indicating a second percentage of the land parcel that was covered by the first plant species at a second time before the first time; and
perform a linear regression analysis on at least one of the percentage, the second percentage, the first time, and the second time to generate the diagnostic model.

25. A system for detecting plant health, the system comprising:
an unmanned aerial vehicle, wherein the unmanned aerial vehicle comprises a camera; and
a computing system comprising one or more computing devices that comprise one or more processors, wherein the computing system is configured to communicate with the unmanned aerial vehicle and configured with specific computer-executable instructions that, when executed by the one or more processors, cause the computing system to:
instruct the unmanned aerial vehicle to capture a first set of images using the camera while flying along a flight path;
receive the first set of images from the unmanned aerial vehicle;
for each image in the first set of images, convert the respective image into a plant health image;
process the plant health images to identify geographic coordinates of one or more pixels that have a value less than a threshold value; and
transmit a message to a controller of an irrigation system to cause the controller to activate a sprinkler at the identified geographic coordinates based on the processing of the plant health images.

26. The system of claim 25, wherein the computer-executable instructions, when executed, further cause the computing system to transmit a second message to the irrigation system to cause the irrigation system to adjust a watering schedule.

27. A system for detecting plant health, the system comprising:
an unmanned aerial vehicle, wherein the unmanned aerial vehicle comprises a camera; and
a computing system comprising one or more computing devices that comprise one or more processors, wherein the computing system is configured to communicate with the unmanned aerial vehicle and configured with specific computer-executable instructions that, when executed by the one or more processors, cause the computing system to:

instruct the unmanned aerial vehicle to capture a first set of images using the camera while flying along a flight path;
receive the first set of images from the unmanned aerial vehicle;
for each image in the first set of images, convert the respective image into a plant health image;
process the plant health images to identify geographic coordinates of a plant that has a canopy percentage that falls below a threshold canopy percentage; and
transmit a message to a lighting system to cause the lighting system to adjust a lighting schedule such that a light corresponding to the identified geographic coordinates is activated for a first period of time instead of a second period of time that is shorter than the first period of time.

28. The system of claim 27, wherein the computer-executable instructions, when executed, further cause the computing system to transmit a second message to the lighting system to cause the lighting system to activate a second light corresponding to the identified geographic coordinates.

* * * * *